United States Patent [19]
Tung et al.

[11] Patent Number: 5,858,982
[45] Date of Patent: Jan. 12, 1999

[54] CATHEPSIN AND METHODS AND COMPOSITIONS FOR INHIBITION THEREOF

[75] Inventors: Jay S. Tung, Belmont; Sukanto Sinha, San Francisco; Christopher M. F. Semko, Fremont, all of Calif.

[73] Assignee: Athena Neurosciences, Inc., South San Francisco, Calif.

[21] Appl. No.: 850,392

[22] Filed: May 2, 1997

Related U.S. Application Data

[63] Continuation of Ser. No. 469,362, Jun. 6, 1995.

[51] Int. Cl.$^6$ ............ A61K 38/00; A61K 38/06
[52] U.S. Cl. ............ 514/19; 514/2; 435/240.2; 530/324
[58] Field of Search ............ 514/2, 19

[56] References Cited

U.S. PATENT DOCUMENTS

| | | | |
|---|---|---|---|
| 4,666,829 | 5/1987 | Glenner et al. | 435/6 |
| 5,011,472 | 4/1991 | Aebisher | 604/50 |
| 5,023,252 | 6/1991 | Hseih | 514/183 |
| 5,164,295 | 11/1992 | Kisilevsky et al. | 435/7 |
| 5,221,607 | 6/1993 | Cordell et al. | 435/6 |
| 5,348,963 | 9/1994 | Gandy et al. | 514/313 |
| 5,441,870 | 8/1995 | Seubert et al. | 435/7 |
| 5,478,857 | 12/1995 | Clemens et al. | 514/381 |
| 5,523,295 | 6/1996 | Fasman | 514/63 |
| 5,523,314 | 6/1996 | Bue-Valleskey et al. | 514/369 |

FOREIGN PATENT DOCUMENTS

| | | |
|---|---|---|
| 95304553 | 6/1995 | European Pat. Off. |
| PCT/US93/01041 | 1/1993 | WIPO |
| WO94/10569 | 5/1994 | WIPO |
| WO95/09838 | 4/1995 | WIPO |
| PCT/US95/06383 | 5/1995 | WIPO |
| PCT/US96/00359 | 1/1996 | WIPO |
| PCT/US96/00360 | 1/1996 | WIPO |
| PCT/US96/01349 | 1/1996 | WIPO |

OTHER PUBLICATIONS

Patel S.V. Pharmacotherapy of cognitive impairment in Alzheimer's disease: a review. J. Geriatr. Psychiatry Neurol. 8, 81–95 (see copy in parent case), 1995.
Glenner et al., *Biochem. Biophys. Res. Commun.* 120:885–890 (1984).
Selkoe, *Neuron* 6:487 (1991).
Goate et al., *Nature* 349:704–706 (1991).
Chartier Harlan et al., *Nature* 353:844–846 (1991).
Murrell et al., *Science* 254:97–99 (1991).
Mullan et al., *Nature Genet* 1:345–347 (1992).
Younkin et al., *Science* 259:514–516 (1993).
Kang et al., *Nature* 325:733–736 (1987).
Ponte et al., *Nature* 331:525–527 (1988).
Tanzi et al., *Nature* 331:528–530 (1988).
Kitaguchi et al., *Nature* 331:530–532 (1988).
Hardy, *Nature Genet.* 1:233–234 (1992).
*J. Gen. Chem. USSR* 34:1021 (1964).
*J. Org. Chem.* 49:2279 (1984).
Luly et al., *Journal of Organic Chemistry*, 52(8):1487 et seq. (1987).
Green et al., J. Biol. Chem., "Peptidyl Diazomethyl Ketones are Specific Inactivators of Thiol Proteinases", 256(4):1923–1928 (1981).
Citron et al., *Nature*, 360:672–674 (1992).
Hansen et al., *J. Immun. Meth.*, 119:203–210 (1989).
Simons et al., *JACS*, 98:7098–7099 (1976).
Frohman et al., (1988), *PNAS USA* 85:8998–9002).
Patel et al., *Psychiatry Neurol.*, 8:81–95 (1995).

*Primary Examiner*—Cecilia J. Tsang
*Assistant Examiner*—Michael Borin
*Attorney, Agent, or Firm*—Burns, Doane, Swecker & Mathis, L.L.P.

[57] ABSTRACT

Methods for inhibiting the secretion of β-amyloid peptide (βAP) from cells comprise administering to the cells certain compounds which inhibit the activity of an approximately 31 kD protease involved in βAP secretion. The 31 kD protease has been designated Cathepsin Y. Screening methods for βAP inhibitors rely on determining the activity of test compounds in the presence of Cathepsin Y and a suitable peptide substrate. This invention is also directed to a nucleic acid sequence that encodes Cathepsin Y and the expression and isolation of Cathepsin Y.

13 Claims, 10 Drawing Sheets

```
GGTAACGCTGGCTCCTGTGAAGGGGGTAATGACCTGTCCGTGTGGGACTACGCCCACCAG
 G  N  A  G  S  C  E  G  G  N  D  L  S  Y  W  D  Y  A  H  Q
━━━━━━━━━━━━━━━━━━━━━━━ Cat Z (+) 3 ━━━━━━━━━━━━━━━━━━━━━━━
━━━━━━━━━━━━━━━━━━━━━━━━ 3'RACE ━━━━━━━━━━━━━━━━━━━━━━━━━━

CACGGCATCCCTGACGAGACCTGCAACAACTACCAGGCCAAGGACCAGGAGTGTGACAAG
         ━━━━━ 1758 ━━━━▶
 H  G  I  P  D  E  T  C  N  N  Y  Q  A  K  D  Q  E  C  D  K
━━━━━━━━━━━━━━━━━━━━━━━ Cat Z (+) 3 ━━━━━━━━━━━━━━━━━━━━━━━
━━━━━━━━━━━━━━━━━━━━━━━━ 3'RACE ━━━━━━━━━━━━━━━━━━━━━━━━━━

EcoRI
                            ┊
TTTAACCAATGTGGGACATGCAATGAATTCAAAGAGTGCCACGCCATCCGGAACTACACC
 F  N  Q  C  G  T  C  N  E  F  K  E  C  H  A  I  R  N  Y  T
━━━━━━━━━━━━━━━━━━━━━━━ Cat Z (+) 3 ━━━━━━━━━━━━━━━━━━━━━━━
━━━━━━━━━━━━━━━━━━━━━━━━ 3'RACE ━━━━━━━━━━━━━━━━━━━━━━━━━━

CTCTGGAGGGTGGGAGACTACGGCTCCCTCTCTGGGAGGGAGAAGATGATGGCAGAAATC
 L  W  R  V  G  D  Y  G  S  L  S  G  R  E  K  M  M  A  E  I
━━━━━━━━━━━━━━━━━━━━━━━ Cat Z (+) 3 ━━━━━━━━━━━━━━━━━━━━━━━
━━━━━━━━━━━━━━━━━━━━━━━━ 3'RACE ━━━━━━━━━━━━━━━━━━━━━━━━━━

Pvu II
                     ┊
TACGCAAATGGTCCCATCAGCTGTGGAATAATGGCAACAGAAAGACTGGCTAACTACACC
 Y  A  N  G  P  I  S  C  G  I  M  A  T  E  R  L  A  N  Y  T
━━━━━━━━━━━━━━━━━━━━━━━ Cat Z (+) 3 ━━━━━━━━━━━━━━━━━━━━━━━
━━━━━━━━━━━━━━━━━━━━━━━━ 3'RACE ━━━━━━━━━━━━━━━━━━━━━━━━━━
```

FIG. 4C

```
GGAGGCATCTATGCCGAATACCAGGACACCACATATATAAACCATGTCGTTTCCGTGGCT
 G  G  I  Y  A  E  Y  Q  D  T  T  Y  I  N  H  V  V  S  V  A
━━━━━━━━━━━━━━━ Cat Z (+) 3 ━━━━━━━━━━━━━━━━
━━━━━━━━━━━━━━━━ 3'RACE ━━━━━━━━━━━━━━━━━━━

EcoRI          NcoI
GGGTGGGGCATCAGTGATGGGACTGAGTACTGGATTGTCCGGAATTCATGGGGTGAACCA
 G  W  G  I  S  D  G  T  E  Y  W  I  V  R  N  S  W  G  E  P
━━━━━━ Cat Z (+) 3 ━━━━━━┥
━━━━━━━━━━━━━━━━ 3'RACE ━━━━━━━━━━━━━━━━━━━

TGGGGCGAGAGAGGCTGGCTGAGGATCGTGACCAGCACCTATAAGGATGGGAAGGGCGCC
 W  G  E  R  G  W  L  R  I  V  T  S  T  Y  K  D  G  K  G  A
━━━━━━━━━━━━━━━━ 3'RACE ━━━━━━━━━━━━━━━━━━━

AGATACAACCTTGCCATCGAGGAGCACTGTACATTTGGGGACCCCATCGTTTAAGGCCAT
 R  Y  N  L  A  I  E  E  H  C  T  F  G  D  P  I  V
━━━━━━━━━━━━━━━━ 3'RACE ━━━━━━━━━━━━━━━━━━━

BamHI
GTCACTAGAAGCGCAGTTTAAGAAAAGGCATGGTGACTCATGACCAGAGGGGATCCTATGG
━━━━━━━━━━━━━━━━ 3'RACE ━━━━━━━━━━━━━━━━━━━

TTATGTGTGCCAGGCTGGCTGGCAGGAACTGGGGTGGCTATCAATATTGGATGGCGAGGAC
━━━━━━━━━━━━━━━━ 3'RACE ━━━━━━━━━━━━━━━━━━━

AGCGTGGTACTGGCTGCGAGTGTTCCTGAGAGTTGAAAGTGGGATGACTTATGACACTTGC
━━━━━━━━━━━━━━━━ 3'RACE ━━━━━━━━━━━━━━━━━━━
```

FIG. 4D

ACAGCATGGCTCTGCCTCACAATGATGCAGTCAGCCACCTGGTGAAGAAGTGACCTGCGAC
━━━━━━━━━━━━━━━━ 3'RACE ━━━━━━━━━━━━━━━━

ACAGGAAACGATGGGACCTCAGTCTTCTTCAGCAGAGGACTTGAWAYTTKGTWTKTGGCMM
━━━━━━━━━━━━━━━━ 3'RACE ━━━━━━━━━━━━━━━━

CTGTGGGCAATAWWWTGGCATTTAAGAGGTGGRAGAGTTCAAACTTATCMCCATTCTTATT
━━━━━━━━━━━━━━━━ 3'RACE ━━━━━━━━━━━━━━━━

TCACYTTAGRATCMAGGGTGGGRGRGRGRGGGAGGGAATTGTCARTTCCCCMTCCCCCCAN
━━━━━━━━━━━━━━━━ 3'RACE ━━━━━━━━━━━━━━━━

TGNTGRAWAAARAATCTGCCCCTYCCCGAAAAAAAAAAAAAAAAAAAAAAAAAAAAAAAAA
━━━━━━━━━━━━━━━━ 3'RACE ━━━━━━━━━━━━━━━━

XbaI
                                                             |
GAAAAAAAAAAAAAAAAAAAAAAAAAAAAAAAAAAAAAAAAAAAACGCTCTAGA
━━━━━━━━━━━━━━━━ 3'RACE ━━━━━━━━━━━━━━━━┥

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Asp  Ala  Glu  Phe  Arg  His  Asp  Ser  Gly  Tyr  Glu  Val  His  His  Gln  Lys
 1                  5                        10                           15

Leu  Val  Phe  Phe  Ala  Glu  Asp  Val  Gly  Ser  Asn  Lys  Gly  Ala  Ile  Ile
               20                       25                      30

Gly  Leu  Met  Val  Gly  Gly  Val  Val  Ile  Ala  Thr
          35                       40
```

( 2 ) INFORMATION FOR SEQ ID NO:2:

( i ) SEQUENCE CHARACTERISTICS:
        ( A ) LENGTH: 1558 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 103..1011

( x i ) SEQUENCE DESCRIPTION: SEQ ID NO:2:

```
GGGCCGAGGC  CGAGGCCGGG  GCGGGATCCA  GAGCGGAAGC  CGGCGCGGGA  TCTGGGACTC        60

GGAGCGGGAT  CCGGAGAGGG  ACCCAGGAGC  CGGCGCGGGG  CC  ATG  GCG  AGG  CGC       114
                                                    Met Ala  Arg  Arg
                                                     1

GGG  CCA  GGG  TGG  CGG  CCG  CTT  CTG  CTG  CTC  GTG  CTG  CTG  GCG  GGC  GCG   162
Gly  Pro  Gly  Trp  Arg  Pro  Leu  Leu  Leu  Leu  Val  Leu  Leu  Ala  Gly  Ala
 5                  10                      15                      20

GCG  CAG  GGC  GGC  CTC  TAC  TTC  CGC  CGG  GGA  CAG  ACC  TGC  TAC  CGG  CCT   210
Ala  Gln  Gly  Gly  Leu  Tyr  Phe  Arg  Arg  Gly  Gln  Thr  Cys  Tyr  Arg  Pro
                    25                      30                      35

CTG  CGG  GGG  GAC  GGG  CTG  GCT  CCG  CTG  GGG  CGC  AGC  ACA  TAC  CCC  CGG   258
Leu  Arg  Gly  Asp  Gly  Leu  Ala  Pro  Leu  Gly  Arg  Ser  Thr  Tyr  Pro  Arg
               40                       45                      50

CCT  CAT  GAG  TAC  CTG  TCC  CCA  GCG  GAT  CTG  CCC  AAG  AGC  TGG  GAC  TGG   306
Pro  His  Glu  Tyr  Leu  Ser  Pro  Ala  Asp  Leu  Pro  Lys  Ser  Trp  Asp  Trp
          55                       60                      65
```

```
CGC  AAT  GTG  GAT  GGT  GTC  AAC  TAT  GCC  AGC  ATC  ACC  CGG  AAC  CAG  CAC        354
Arg  Asn  Val  Asp  Gly  Val  Asn  Tyr  Ala  Ser  Ile  Thr  Arg  Asn  Gln  His
     70                  75                       80

ATC  CCC  CAA  TAC  TGC  GGC  TCC  TGC  TGG  GCC  CAC  GCC  AGC  ACC  AGC  GCT        402
Ile  Pro  Gln  Tyr  Cys  Gly  Ser  Cys  Trp  Ala  His  Ala  Ser  Thr  Ser  Ala
85                       90                       95                           100

ATG  GCG  GAT  CGG  ATC  AAC  ATC  AAG  AGG  AAG  GGA  GCG  TGG  CCC  TCC  ACC        450
Met  Ala  Asp  Arg  Ile  Asn  Ile  Lys  Arg  Lys  Gly  Ala  Trp  Pro  Ser  Thr
                    105                      110                      115

CTC  CTG  TCC  GTG  CAG  AAC  GTC  ATC  GAC  TGC  GGT  AAC  GCT  GGC  TCC  TGT        498
Leu  Leu  Ser  Val  Gln  Asn  Val  Ile  Asp  Cys  Gly  Asn  Ala  Gly  Ser  Cys
               120                      125                      130

GAA  GGG  GGT  AAT  GAC  CTG  TCC  GTG  TGG  GAC  TAC  GCC  CAC  CAG  CAC  GGC        546
Glu  Gly  Gly  Asn  Asp  Leu  Ser  Val  Trp  Asp  Tyr  Ala  His  Gln  His  Gly
          135                      140                      145

ATC  CCT  GAC  GAG  ACC  TGC  AAC  AAC  TAC  CAG  GCC  AAG  GAC  CAG  GAG  TGT        594
Ile  Pro  Asp  Glu  Thr  Cys  Asn  Asn  Tyr  Gln  Ala  Lys  Asp  Gln  Glu  Cys
     150                      155                      160

GAC  AAG  TTT  AAC  CAA  TGT  GGG  ACA  TGC  AAT  GAA  TTC  AAA  GAG  TGC  CAC        642
Asp  Lys  Phe  Asn  Gln  Cys  Gly  Thr  Cys  Asn  Glu  Phe  Lys  Glu  Cys  His
165                      170                      175                      180

GCC  ATC  CGG  AAC  TAC  ACC  CTC  TGG  AGG  GTG  GGA  GAC  TAC  GGC  TCC  CTC        690
Ala  Ile  Arg  Asn  Tyr  Thr  Leu  Trp  Arg  Val  Gly  Asp  Tyr  Gly  Ser  Leu
                    185                      190                      195

TCT  GGG  AGG  GAG  AAG  ATG  ATG  GCA  GAA  ATC  TAC  GCA  AAT  GGT  CCC  ATC        738
Ser  Gly  Arg  Glu  Lys  Met  Met  Ala  Glu  Ile  Tyr  Ala  Asn  Gly  Pro  Ile
               200                      205                      210

AGC  TGT  GGA  ATA  ATG  GCA  ACA  GAA  AGA  CTG  GCT  AAC  TAC  ACC  GGA  GGC        786
Ser  Cys  Gly  Ile  Met  Ala  Thr  Glu  Arg  Leu  Ala  Asn  Tyr  Thr  Gly  Gly
          215                      220                      225

ATC  TAT  GCC  GAA  TAC  CAG  GAC  ACC  ACA  TAT  ATA  AAC  CAT  GTC  GTT  TCC        834
Ile  Tyr  Ala  Glu  Tyr  Gln  Asp  Thr  Thr  Tyr  Ile  Asn  His  Val  Val  Ser
     230                      235                      240

GTG  GCT  GGG  TGG  GGC  ATC  AGT  GAT  GGG  ACT  GAG  TAC  TGG  ATT  GTC  CGG        882
Val  Ala  Gly  Trp  Gly  Ile  Ser  Asp  Gly  Thr  Glu  Tyr  Trp  Ile  Val  Arg
245                      250                      255                      260

AAT  TCA  TGG  GGT  GAA  CCA  TGG  GGC  GAG  AGA  GGC  TGG  CTG  AGG  ATC  GTG        930
Asn  Ser  Trp  Gly  Glu  Pro  Trp  Gly  Glu  Arg  Gly  Trp  Leu  Arg  Ile  Val
                    265                      270                      275

ACC  AGC  ACC  TAT  AAG  GAT  GGG  AAG  GGC  GCC  AGA  TAC  AAC  CTT  GCC  ATC        978
Thr  Ser  Thr  Tyr  Lys  Asp  Gly  Lys  Gly  Ala  Arg  Tyr  Asn  Leu  Ala  Ile
               280                      285                      290

GAG  GAG  CAC  TGT  ACA  TTT  GGG  GAC  CCC  ATC  GTT  TAAGGCCATG TCACTAGAAG         1031
Glu  Glu  His  Cys  Thr  Phe  Gly  Asp  Pro  Ile  Val
          295                      300

CGCAGTTTAA GAAAAGGCAT GGTGACTCAT GACCAGAGGG GATCCTATGG TTATGTGTGC                    1091

CAGGCTGGCT GGCAGGAACT GGGGTGGCTA TCAATATTGG ATGGCGAGGA CAGCGTGGTA                    1151

CTGGCTGCGA GTGTTCCTGA GAGTTGAAAG TGGGATGACT TATGACACTT GCACAGCATG                    1211

GCTCTGCCTC ACAATGATGC AGTCAGCCAC CTGGTGAAGA AGTGACCTGC GACACAGGAA                    1271

ACGATGGGAC CTCAGTCTTC TTCAGCAGAG GACTTGAWAY TTKGTWTKTG GCMMCTGTGG                    1331

GCAATAWWWT GGCATTTAAG AGGTGGGAGA GTTCAAACTT ATCMCCATTC TTATTTCACY                    1391

TTAGRATCMA GGGTGGGRGR GRGRGGGAGG GAATTGTCAR TTCCCCMTCC CCCCANTGNT                    1451

GRAWAAARAA TCTGCCCCTY CCCGAAAAAA AAAAAAAAAA AAAAAAAAAA AAAAAGAAA                     1511

AAAAAAAAAA AAAAAAAAAA AAAAAAAAAA AAAAAAACG CTCTAGA                                   1558
```

-continued ( 2 ) INFORMATION FOR SEQ ID NO:3:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Ala Arg Arg Gly Pro Gly Trp Arg Pro Leu Leu Leu Leu Val Leu
 1               5                  10                  15
Leu Ala Gly Ala Ala Gln Gly Gly Leu Tyr Phe Arg Arg Gly Gln Thr
            20                  25                  30
Cys Tyr Arg Pro Leu Arg Gly Asp Gly Leu Ala Pro Leu Gly Arg Ser
        35                  40                  45
Thr Tyr Pro Arg Pro His Glu Tyr Leu Ser Pro Ala Asp Leu Pro Lys
    50                  55                  60
Ser Trp Asp Trp Arg Asn Val Asp Gly Val Asn Tyr Ala Ser Ile Thr
65                  70                  75                  80
Arg Asn Gln His Ile Pro Gln Tyr Cys Gly Ser Cys Trp Ala His Ala
                85                  90                  95
Ser Thr Ser Ala Met Ala Asp Arg Ile Asn Ile Lys Arg Lys Gly Ala
            100                 105                 110
Trp Pro Ser Thr Leu Leu Ser Val Gln Asn Val Ile Asp Cys Gly Asn
        115                 120                 125
Ala Gly Ser Cys Glu Gly Gly Asn Asp Leu Ser Val Trp Asp Tyr Ala
    130                 135                 140
His Gln His Gly Ile Pro Asp Glu Thr Cys Asn Asn Tyr Gln Ala Lys
145                 150                 155                 160
Asp Gln Glu Cys Asp Lys Phe Asn Gln Cys Gly Thr Cys Asn Glu Phe
                165                 170                 175
Lys Glu Cys His Ala Ile Arg Asn Tyr Thr Leu Trp Arg Val Gly Asp
            180                 185                 190
Tyr Gly Ser Leu Ser Gly Arg Glu Lys Met Met Ala Glu Ile Tyr Ala
        195                 200                 205
Asn Gly Pro Ile Ser Cys Gly Ile Met Ala Thr Glu Arg Leu Ala Asn
    210                 215                 220
Tyr Thr Gly Gly Ile Tyr Ala Glu Tyr Gln Asp Thr Thr Tyr Ile Asn
225                 230                 235                 240
His Val Val Ser Val Ala Gly Trp Gly Ile Ser Asp Gly Thr Glu Tyr
                245                 250                 255
Trp Ile Val Arg Asn Ser Trp Gly Glu Pro Trp Gly Glu Arg Gly Trp
            260                 265                 270
Leu Arg Ile Val Thr Ser Thr Tyr Lys Asp Gly Lys Gly Ala Arg Tyr
        275                 280                 285
Asn Leu Ala Ile Glu Glu His Cys Thr Phe Gly Asp Pro Ile Val
    290                 295                 300
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7

(D) OTHER INFORMATION: /note= "This position is Gly or Asp."

(ix) FEATURE:
(A) NAME/KEY: Modified-site
(B) LOCATION: 8
(D) OTHER INFORMATION: /note= "This position is Asn or Val."

(ix) FEATURE:
(A) NAME/KEY: Modified-site
(B) LOCATION: 14
(D) OTHER INFORMATION: /note= "This position is Val or Asn."

(ix) FEATURE:
(A) NAME/KEY: Modified-site
(B) LOCATION: 20
(D) OTHER INFORMATION: /note= "This position is Arg or Thr."

(xi) SEQUENCE DESCRIPTION: SEQ ID NO:4:

Ser Leu Pro Lys Ser Trp Xaa Xaa Arg Asn Val Asp Gly Xaa Asn Tyr
1               5                   10                  15

Ala Ser Ile Xaa
        20

(2) INFORMATION FOR SEQ ID NO:5:

(i) SEQUENCE CHARACTERISTICS:
(A) LENGTH: 11 amino acids
(B) TYPE: amino acid
(C) STRANDEDNESS: single
(D) TOPOLOGY: linear (xi) SEQUENCE DESCRIPTION: SEQ ID NO:5:

Leu Phe Tyr Asp Gln Ser Pro Thr Ala Thr Ile
1               5                   10

(2) INFORMATION FOR SEQ ID NO:6:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:6:

Tyr Lys Arg Asp Met Val Gly Gly Val Val Ile Ala
1               5                   10

(2) INFORMATION FOR SEQ ID NO:7:

(i) SEQUENCE CHARACTERISTICS:
(A) LENGTH: 11 amino acids
(B) TYPE: amino acid
(C) STRANDEDNESS: single
(D) TOPOLOGY: linear (xi) SEQUENCE DESCRIPTION: SEQ ID NO:7:

Glu Gly Tyr Tyr Gly Asn Tyr Gly Val Tyr Ala
1               5                   10

(2) INFORMATION FOR SEQ ID NO:8:

(i) SEQUENCE CHARACTERISTICS:
(A) LENGTH: 12 amino acids
(B) TYPE: amino acid
(C) STRANDEDNESS: single
(D) TOPOLOGY: linear ( x i ) SEQUENCE DESCRIPTION: SEQ ID NO:8:

Phe Phe Asp Glu Pro Asn Pro Gly Val Thr Ile Tyr
1               5                   10

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(18, "")
        ( D ) OTHER INFORMATION: /note= "This position is inosine."

( x i ) SEQUENCE DESCRIPTION: SEQ ID NO:9:

TGTACCCGGG CVYARCANGA WCCG                                           24

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is Tyr or
            Trp."

( x i ) SEQUENCE DESCRIPTION: SEQ ID NO:10:

Cys Gly Ser Cys Xaa
1               5

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(13, "")
        ( D ) OTHER INFORMATION: /note= "This position is inosine."

( x i ) SEQUENCE DESCRIPTION: SEQ ID NO:11:

CGTAGGATCC CTNCCNAARA GCTGG                                          25

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

Ser Leu Pro Lys Ser Trp
1               5

( 2 ) INFORMATION FOR SEQ ID NO:13:

( i ) SEQUENCE CHARACTERISTICS:
        ( A ) LENGTH: 24 base pairs (B) TYPE: nucleic acid
            (C) STRANDEDNESS: single
            (D) TOPOLOGY: linear (xi) SEQUENCE DESCRIPTION: SEQ ID NO:13:

GACTGAATTC TTNACNAGCC AGTA  24

(2) INFORMATION FOR SEQ ID NO:14:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:14:

GGAAACAGCT ATGACCATGA T  21

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:15:

CCCTCACTAA AGGGAACA  18

(2) INFORMATION FOR SEQ ID NO:16:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:16:

GGACTCGAGT CGACTCTAGA GCGTTTTTTT TTTTTTTTT T  41

(2) INFORMATION FOR SEQ ID NO:17:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:17:

GACTCGAGTC GACTCTAGAG CGT  23

(2) INFORMATION FOR SEQ ID NO:18:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:18:

CACGAATTCA CTATCGATTC TGGAACCTTC AGAGG  35

(2) INFORMATION FOR SEQ ID NO:19:

(i) SEQUENCE CHARACTERISTICS:
            (A) LENGTH: 38 base pairs
            (B) TYPE: nucleic acid
            (C) STRANDEDNESS: single (D) TOPOLOGY: linear (xi) SEQUENCE DESCRIPTION: SEQ ID NO:19:

CTGGTTCGGC CCACCTCTGA AGGTTCCAGA ATCGATAG                      38

(2) INFORMATION FOR SEQ ID NO:20:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (xi) SEQUENCE DESCRIPTION: SEQ ID NO:20:

CAGGAGGGTG GAGGGCCACG CTCCCT                                    26

CATHEPSIN AND METHODS AND COMPOSITIONS FOR INHIBITION THEREOF

This application is a continuation, of application Ser. No. 08/469,362, filed Jun. 6, 1995.

BACKGROUND OF THE INVENTION

1. Field of the Invention

This invention relates generally to methods and compositions for inhibiting β-amyloid peptide (βAP) production in cells. In particular, this invention relates to compounds which are capable of inhibiting the intracellular production of βAP, and the use of such compounds in methods for inhibiting βAP production.

This invention also relates to an isolated novel protein, Cathepsin Y, which is a novel carboxypeptidase involved in the generation of βAP. Methods for isolation of this protein are provided. DNA isolates coding for Cathepsin Y and methods of obtaining such DNA are provided, together with expression systems for recombinant production of Cathepsin Y useful in therapeutic or diagnostic compositions.

2. State of the Art

Alzheimer's Disease (AD) is a degenerative brain disorder characterized clinically by progressive loss of memory, cognition, reasoning, judgment and emotional stability that gradually leads to profound mental deterioration and, ultimately, death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restricted anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neuro-surgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. βAP is a fragment of a large membrane-spanning glycoprotein, referred to herein as the β-amyloid precursor protein (APP), comprising approximately 39–43 amino acid residues. This protein fragment was first purified, and a partial amino acid sequence was reported in, Glenner and Wong, *Biochem. Biophys. Res. Commun.* 120:885–890 (1984). The isolation procedure and the sequence data for the first 28 amino acids are described in U.S. Pat. No. 4,666,829.

βAP is further characterized by its relative mobility in SDS-polyacrylamide gel electrophoresis or high performance liquid chromatography (HPLC). βAP can occur in a filamentous polymeric form which exhibits the Congo-red and thioflavin-S dye-binding characteristics of amyloid. βAP can also occur in a non-filamentous form ("preamyloid" or "amorphous" or "diffuse" deposits) in tissue, in which form no detectable birefringent staining by Congo red occurs. A portion of this protein in the insoluble form obtained from meningeal blood vessels is described in U.S. Pat. No. 4,666,829.

APP is normally produced by cells in many tissues of various animals, including humans. APP is encoded by a gene on the long arm of human chromosome 21. Knowledge of the structure of the gene encoding APP has indicated that βAP arises as a peptide fragment from cleavage of APP by at least one heretofore unidentified protease. This cleavage appears to occur in the lysosomes. The precise biochemical pathway by which the βAP fragment is cleaved from the APP and subsequently deposited as amyloid plaques is still under investigation.

Several lines of evidence indicate that progressive cerebral deposition of βAP plays a seminal role in the pathogenesis of AD and can precede cognitive symptoms by years or decades (for a review, see Selkoe, (1991) *Neuron* 6:487). Recently, it has been shown that βAP is released from neural cells grown in culture as well as into cerebral spinal fluid of both normal individuals and AD patients.

Certain inherited mutations which occur in the APP gene are also known to cause AD and AD-related conditions. For example, mis-sense DNA mutations at amino acid 717 of the 770-amino acid isoform of APP can be found in affected members but not in unaffected members of several families with a genetically determined (familial) form of AD (Goate et al., *Nature* 349:704–706 (1991); Chartier Harlan et al., *Nature* 353:844–846 (1991); and Murrell et al., (1991) *Science* 254:97–99). A double mutation changing lysine$^{595}$-methionine$^{596}$ to asparagine$^{595}$-leucinell$^{596}$ (with reference to the 695-amino acid isoform of APP) found in a Swedish family was reported in 1992 (Mullan et al., (1992) *Nature Genet* 1:345–347) and is referred to as the Swedish variant or mutation.

Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the βAP deposition disease, HCHWA-D, and a change from alanine to glycine at amino acid 692 appears to cause a phenotype that resembles AD in some patients but HCHWA-D in others. See, Younkin, et al., *Science* 259:514–516 (1993).

Despite the progress which has been made in understanding underlying mechanisms of AD and other βAP-related diseases, there remains a need to develop compositions and methods for treatment of the disease(s).

SUMMARY OF THE INVENTION

This invention is directed, in part, to methods for inhibiting β-amyloid peptide production in cells producing β-amyloid peptide. Specifically, the methods of this invention are directed, in part, to the discovery that specific compounds, as defined below, are effective in inhibiting β-amyloid peptide production in cells expressing β-amyloid peptide. Because β-amyloid peptide production is associated with deposition of amyloid plaques in mammals and Alzheimer's disease in humans, the compounds described herein are also useful in inhibiting deposition of such plaques and in treating Alzheimer's disease.

This invention is further directed, in part, to the identification of a novel protease, Cathepsin Y, and to nucleic acids which encode this protease. This invention is also directed to methods for the recombinant expression of Cathepsin Y.

Accordingly, in one of its method aspects, this invention is directed to a method of inhibiting β-amyloid peptide production in cells producing β-amyloid peptide, comprising administering to such cells an inhibitory amount of a compound of formula I:

wherein:
R is selected from the group consisting hydrogen, alkyl of from 1 to 6 carbon atoms, and where R and $R^2$ are joined to form a ring structure of from 4 to 10 carbon atoms, R' is selected from the group consisting hydrogen, alkyl of from 1 to 6 carbon atoms and where R' and $R^3$ are joined to form a ring structure of from 4 to 10 carbon atoms, $R^1$ is selected from the group consisting of
  alkyl of from 1 to 4 carbon atoms substituted with from 1 to 5 substituents selected from the group consisting of (a) aryl of from 6 to 10 carbon atoms, (b) aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, (c) cycloalkyl of from 3 to 8 carbon atoms and (d) heterocycles of from 3 to 14 carbon atoms having from 1 to 3 heteroatoms selected from the group consisting of nitrogen, oxygen and sulfur
  wherein said substituted alkyl group is optionally further substituted with from 1 to 2 hydroxyl groups,
  alkenyl of from 2 to 4 carbon atoms substituted with from 1 to 4 substituents selected from the group consisting of (a) aryl of from 6 to 10 carbon atoms, (b) aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, (c) cycloalkyl of from 3 to 8 carbon atoms and (d) heterocycles of from 3 to 14 carbon atoms having from 1 to 3 heteroatoms selected from the group consisting of nitrogen, oxygen and sulfur,
  aryl of from 6 to 10 carbon atoms,
  aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino,
  fluorenyl,
  heterocycles of from 3 to 14 carbon atoms having from 1 to 3 heteroatoms selected from the group consisting of nitrogen, oxygen and sulfur;

$R^2$ and $R^3$ are independently D- or L-amino acid side chains of at least 2 carbon atoms with the proviso that said amino acid side chains do not include the proline side chain;

$R^4$ is selected from the group consisting of
  —C(O)CH=N=N,
  —CH$_2$OH,
  —C=NOH, and
  —C(O)$R^5$ where $R^5$ is hydrogen, alkyl of from 1 to 6 carbon atoms, haloalkyl of from 1 to 6 carbon atoms and 1 to 2 halo groups, alkoxy of from 1 to 6 carbon atoms, —NR$^6$R$^7$ where $R^6$ and $R^7$ are independently selected from the group consisting of hydrogen and alkyl of from 1 to 6 carbon atoms, and —N(CH$_3$)OCH$_3$;

X is selected from the group consisting of —O—, —NR$^9$—, and —S— where $R^9$ is selected from the group consisting of hydrogen, alkyl of from 1 to 6 carbon atoms and aryl of from 6 to 10 carbon atoms;

Y is selected from the group consisting of —C(O)— and —C(S)—;

m is equal to zero or one; and n is equal to zero to two, or pharmaceutically acceptable salts thereof with the proviso that when $R^1$ is 1-naphthyl, $R^2$ is —CH(CH$_3$)$_2$ (L-isomer), $R^3$ is —CH$_2$φ (L-isomer), Y is —C(O)—, m is zero and n is one, then $R^4$ is not —N(CH$_3$)OCH$_3$, with the further proviso that when $R^1$ is diphenylmethyl, $R^2$ is p-(benzyloxy)benzyl (L-isomer), Y is —C(O)—, and m and n are zero, then $R^4$ is not —N(CH$_3$)OCH$_3$, and with still the further proviso that when $R^1$ is (1,2-diphenyl)ethenyl, Y is —C(O)—, $R^2$ is —CH$_2$φ (L-isomer), and m and n are zero, the $R^4$ is not —N(CH$_3$)OCH$_3$.

In another of its method aspects, this invention is directed to a method of inhibiting the deposition of amyloid plaque in a mammal, comprising administering to such a mammal an effective amount of a compound of formula I above.

In still another of its method aspects, this invention is directed to a method of preventing, treating or inhibiting the onset of Alzheimer's disease (AD) in a mammal which comprises administering to such a mammal an effective amount of a compound of formula I above.

Preferred compounds for use in the methods described herein include, by way of example, the following compounds as defined by formula II below, including all isomers thereof, wherein the amino acid side chain for $R^2$ and $R^3$ is indicated beneath the $R^2$ and $R^3$ substituent:

$$R^1(X)_m-Y-NHCH\underset{\underset{R^2}{|}}{}-\left[\underset{\underset{R^3}{|}}{\overset{\overset{O}{\|}}{C}NH\,CH}\right]_n-R^4 \quad II$$

| R¹ | X | m | Y | R² | n | R³ | R⁴ |
|---|---|---|---|---|---|---|---|
| φ-CH₂— | O | 1 | —C(O)— | —CH(CH₃)₂ (valine) | 1 | —CH₂-φ (phenylalanine) | —C(O)CH=N=N |
| φ-CH₂— | O | 1 | —C(O)— | —CH₂CH(CH₃)₂ (leucine) | 1 | —CH₂-φ (phenylalanine) | —C(O)CH=N=N |
| (φ)₂-CH— | — | 0 | —C(O)— | —CH₂-φ (phenylalanine) | 0 | — | —C(O)H |
| φ-(CH₂)₄— | — | 0 | —C(O)— | —CH₂-φ (phenylalanine) | 0 | — | —C(O)H |
| (φ)₃-C— | — | 0 | —C(O)— | —CH₂-φ (phenylalanine) | 0 | — | —C(O)H |
| (φ)₂CH— | — | 0 | —C(O)— | —CH₂CH₂-φ (homophenylalanine) | 0 | — | —C(O)H |
| φCH=C(φ) | — | 0 | —C(O)— | —CH₂-φ (phenylalanine) | 0 | — | —C(O)H |
| (φ)₂-CH— | — | 0 | —C(O)— | —CH₂-(3-indolyl) (tryptophan) | 0 | — | —C(O)H |
| φ-CH₂— | O | 1 | —C(O)— | —CH₂φ (phenylalanine) | 1 | —CH(CH₃)₂ (valine) | —C(O)H |
| φ-CH₂— | O | 1 | —C(O)— | —CH(CH₃)₂ (valine) | 1 | —CH₂CH(CH₃)₂ (leucine) | —C(O)H |

In one of its product aspects, this invention is directed to an isolated and purified polypeptide having the enzymatic activity of Cathepsin Y protein.

In another of its product aspects, this invention is directed to a purified and isolated nucleic acid sequence which sequence encodes for Cathepsin Y.

In still another of its product aspects, this invention is directed to a purified and isolated nucleic acid sequence capable of hybridizing to Cathepsin Y comprising:

a) a nucleic acid sequence substantially homologous to the nucleic acid sequence of FIG. 4, wherein T can also be U, b) a nucleic acid sequence substantially complementary to the sequence of FIG. 4, wherein T can also be U, or c) fragments of the nucleic acid sequence of FIG. 4, wherein T can also be U or nucleic acid sequences complementary to the sequence in FIG. 4, that are at least 12 bases in length and that do not hybridize to the nucleic acid sequences encoding Cathepsin genes other than Cathepsin Y but which will selectively hybridize DNA encoding Cathepsin Y.

In another of its method aspects, this invention is directed to a method for expressing Cathepsin Y which method comprises transfecting a host cell with a nucleic acid sequence which sequence encodes for Cathepsin Y, culturing the transfected cell under conditions which express Cathepsin Y and recovering Cathepsin Y from the cell culture.

In another of its method aspects, this invention is directed to a method of detecting the expression of Cathepsin Y comprising a) isolating RNA from a mammalian tissue or cell, b) hybridizing to the isolated RNA a labelled nucleic acid sequence capable of hybridizing to Cathepsin Y comprising i) a nucleic acid sequence substantially homologous to the nucleic acid sequence of FIG. 4, wherein T can also be U, ii) nucleic acid sequences substantially complementary to the sequence of FIG. 4, wherein T can also be U, or iii) fragments of the nucleic acid sequence of FIG. 4, wherein T can also be U or nucleic acid sequences complementary to the sequence in FIG. 4, that are at least 12 bases in length and that do not hybridize to nucleic acid sequences of other cathepsin genes but which will selectively hybridize to mammalian DNA encoding Cathepsin Y.

c) determining whether the labelled nucleic acid sequence binds to the isolated RNA.

BRIEF DESCRIPTION OF THE DRAWING

FIGS. 4A–4E depicts the amino acid (SEQ ID NO:3) and DNA sequence (SEQ ID NO:2) of human Cathepsin Y.

DESCRIPTION OF THE PREFERRED EMBODIMENTS

Figure 1:
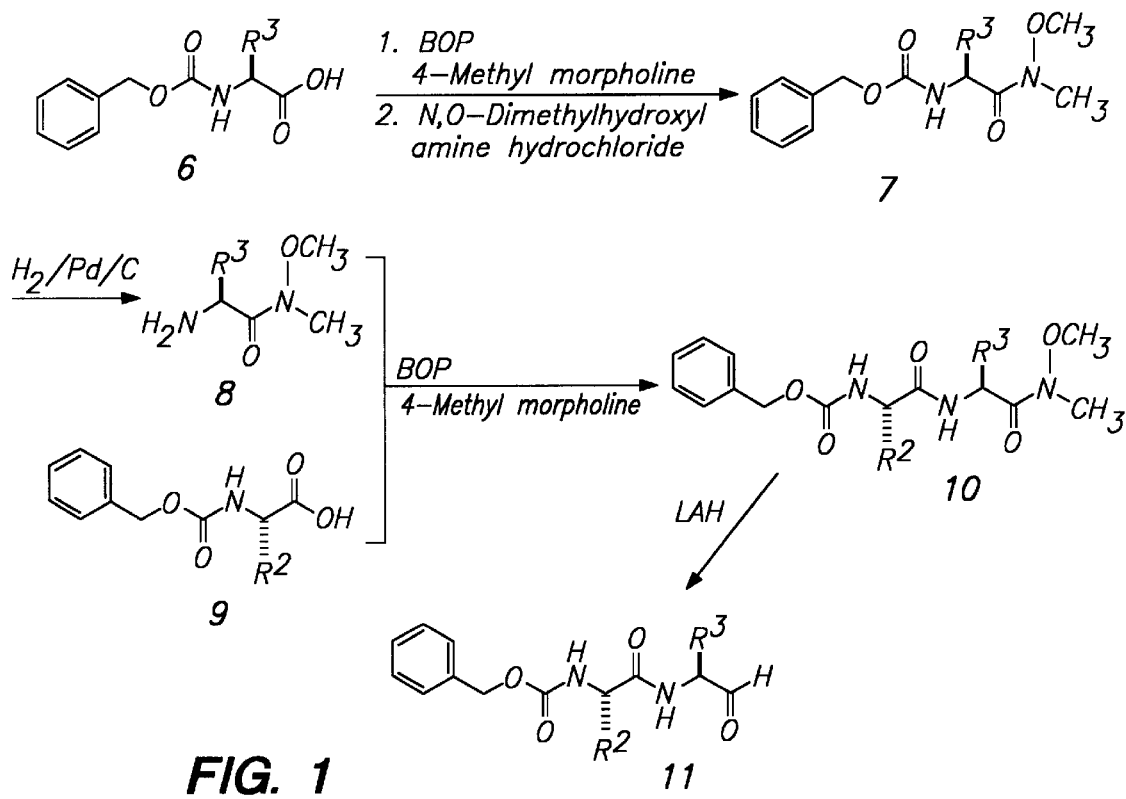
FIGS. 1 and 2 illustrate reaction schemes used to prepare some of the compounds described herein.

This invention is directed, in part, to the inhibition of β-amyloid peptide production in cells producing β-amyloid peptide by administering specific compounds to the cells which inhibition can be employed to retard deposition of amyloid plaques and to treat Alzheimer's disease in mammals.

This invention is also directed in part to the identification of a novel protein, Cathepsin Y, and to nucleic acids which encode this protein. This invention is also directed to methods for the recombinant expression of Cathepsin Y.

However, prior to discussing this invention in further detail, the following terms will first be defined:

Definitions

The following terms and phrases set forth in the specification and claims are defined as follows.

The term "β-amyloid peptide (βAP)" as used herein refers to an approximately 4.2 kD protein which, in the brains of subjects suffering from AD, Down's Syndrome, HCHWA-D and some normal aged subjects, forms a subunit of the amyloid filaments comprising the senile (amyloid) plaques and the amyloid deposits in small cerebral and meningeal blood vessels (amyloid angiopathy). βAP can occur in a filamentous polymeric form (in this form, it exhibits the Congo-red and thioflavin-S dye-binding characteristics of amyloid). βAP can also occur in a non-filamentous form ("preamyloid" or "amorphous" or "diffuse" deposits) in tissue, in which form no detectable birefringent staining by Congo red occurs. A portion of this protein in the insoluble form obtained from meningeal blood vessels is described in U.S. Pat. No. 4,666,829, the full disclosure of which is incorporated herein by reference.

"βAP" as used herein specifically refers to an approximately 39–43 amino acid peptide that is substantially homologous to the form of the peptide produced by the method described in the '829 patent, but which can also be found in soluble form in the extracellular fluid (conditioned medium) of cultured cells grown in vitro and in body fluids of humans and other mammals, including both normal individuals and individuals suffering from βAP-related conditions. Thus, βAP also refers to related βAP sequences that result from mutations in the βAP region of the normal gene. In whatever form, βAP is an approximately 39–43 amino acid fragment of a large membrane-spanning glycoprotein, referred to as the β-amyloid precursor protein (APP), encoded by a gene on the long arm of human chromosome 21. βAP is further characterized by its relative mobility in SDS-polyacrylamide gel electrophoresis or in high performance liquid chromatography. The 43-amino βAP acid sequence (SEQ ID No. 1) is:

$\overset{1}{\text{Asp}}$ Ala Glu Phe Arg His Asp Ser Gly Tyr $\overset{11}{\text{Glu}}$ Val His His Gln Lys Leu Val Phe Phe $\overset{21}{\text{Ala}}$ Glu Asp Val Gly Ser Asn Lys Gly Ala $\overset{31}{\text{Ile}}$ Ile Gly Leu Met Val Gly Gly Val Val $\overset{41}{\text{Ile}}$ Ala Thr βAP also refers to sequences that are substantially homologous to this 43-amino acid sequence.

The term "β-amyloid precursor protein" (APP) as used herein is defined as a polypeptide that is encoded by a gene of the same name localized in humans on the long arm of chromosome 21 which includes βAP within the carboxyl one-third of its length. APP is a glycosylated, single-membrane-spanning protein expressed in a wide variety of cells in many mammalian tissues. Examples of specific isotypes of APP which are currently known to exist in humans are the 695-amino acid polypeptide described by Kang et al., *Nature* 325:733–736 (1987) which is designated as the "normal" APP; the 751-amino acid polypeptide described by Ponte et al., *Nature* 331:525–527 and Tanzi et al., *Nature* 331:528–530 (1988); and the 770-amino acid polypeptide described by Kitaguchi et al., *Nature* 331:530–532 (1988). Examples of specific variants of APP include point mutations which can differ in both position and phenotype (for review of known variant mutations see Hardy, *Nature Genet.* 1:233–234 (1992)).

The term "βAP-related conditions" as used herein is defined as including Alzheimer's disease (which includes familial Alzheimer's disease), Down's Syndrome, HCHWA-D, and advanced aging of the brain.

The terms "conditioned culture medium" and "culture medium" as used herein refer to the aqueous extracellular fluid which surrounds cells grown in tissue culture (in vitro) and which contains, among other constituents, proteins and peptides secreted by the cells.

The term "body fluid" as used herein refers to those fluids of a mammalian host which may contain measurable amounts of βAP and βAP fragments, specifically including blood, cerebrospinal fluid (CSF), urine, and peritoneal fluid. The term "blood" refers to whole blood, as well as blood plasma and serum.

The term "Swedish mutation" refers to a mutation in the human gene encoding APP which results in an inherited, familial form of Alzheimer's disease. The mutation occurs at $LYS_{595}$-$MET_{596}$ of the normal APP gene, where a substitution to $ASN_{595}$-$LEU_{596}$ occurs. It has been found that human cell lines transfected with this mutation will overproduce βAP, secreting the βAP into the conditioned culture medium.

The term "heterocycles containing from 3 to 14 carbon atoms and 1 to 3 hetereoatoms selected from the group consisting of nitrogen, oxygen and sulfur" refers to saturated and unsaturated heterocyclic groups having the requisite number of carbon atoms and heteroatoms. Suitable heterocyclic groups include, by way of example, furazanyl, furyl, imidazolidinyl, imidazolyl, imidazolinyl, indolyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, quinoxalinyl, thiadiazolyl, thiazolyl, thienyl, thiomorpholinyl (e.g. thiomorpholino), triazolyl, and xanthanilyl. These heterocyclic groups can be substituted or unsubstituted. Where the heterocyclic group is substituted, the substituents are selected from alkyl of from 1 to 6 carbon atoms, alkoxy of from 1 to 6 carbon atoms, aryl of from 6 to 10 carbon atoms, aryloxy of from 6 to 10 carbon atoms, and halo.

Preferred heterocycles include well known cyclic aromatic groups containing heteroatoms within the cyclic structure. Such groups include, by way of example, furyl, imidazolyl, oxazolyl, pyrazolyl, pyridyl, pyrimidinyl, thiazolyl, and triazolyl.

The term "alkyl" refers to straight and branched chain alkyl groups such as methyl, ethyl, n-propyl, iso-propyl, n-butyl, tert-butyl, sec-butyl, iso-butyl, n-pentyl, n-hexyl, 2-methylpentyl, and the like; whereas the term "alkoxy" refers to —O—alkyl substituents.

The term "aryl" refers to aromatic substituents comprising carbon and hydrogen such as phenyl, naphthyl and the like whereas the term aryloxy refers to —O—aryl substituents where aryl is as defined above.

The term "halo" or "halogen" refers to fluorine, chlorine, bromine and iodine and preferably fluorine and chlorine.

The term "pharmaceutically acceptable salts" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate salts, and the like. The particular salt employed is not critical.

The term "DNA" refers to deoxyribonucleic acid. The term "RNA" refers to ribonucleic acid.

Naturally occurring amino acid residues in peptides described herein are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Naturally occurring nucleosides in nucleic acids described herein are abbreviated as recommended by the IUPAC-IUB Biological Nomenclature Commission as follows: Adenosine is A; Guanosine is G; Cytidine is C; Thymidine is T and Uridine is U. The abbreviation where the nucleotides are either Cytidine or Thymidine (Uridine) is Y; Adenosine or Guanosine is R; Adenosine or Thymidine (Uridine) is W; Adenosine or Cytidine is M; and Guanosine or Thymidine (Uridine) is K.

The term "Cathepsin Y" as used herein is defined as a polypeptide that is encoded by a gene of the same name. Cathepsin Y is a carboxypeptidase having a molecular weight of approximately 31 kD. Cathepsin Y is able to cleave carboxy-terminal amino acids, with particular activity against aliphatic carboxy-terminal amino acids. Preferably, Cathepsin Y is a polypeptide having a qualitative biological activity in common with the Cathepsin Y of FIGS. 4A–4E and which is greater than about 70% homologous, more preferably greater than 85% homologous and most preferably greater than 90% homologous with the Cathepsin Y sequence of FIGS. 4A–4E. It is contemplated that the Cathepsin Y of the present invention may be substantially homologous to the sequence of FIGS. 4A–4E, typically being greater than 90% homologous, preferably greater than 95% homologous and sometime greater than 99% homologous provided that the Cathepsin Y retains at least a portion of biological activity of the Cathepsin Y of FIGS. 4A–4E.

Included within the scope of term "Cathepsin Y" as that term is used herein are proteins having the amino acid sequence as set forth in FIGS. 4A–4E, deglycosylated or unglycosylated derivatives of the sequence in FIGS. 4A–4E, and homologous generated variants and derivatives of Cathepsin Y, provided that the modifications do not destroy the biological activity in common with the Cathepsin Y of FIGS. 4A–4E.

"Homologous" is defined as the percentage of residues in the candidate sequence that are identical with the residues in the disclosed sequence after aligning the sequences and introducing gaps, if necessary, to achieve the maximum percent homology. A nucleic acid sequence is substantially homologous to the nucleic acid sequence of the disclosed sequence, where it is greater than 80% homologous, preferably greater than 90% homologous and most preferably greater than 95% homologous.

"Complementary" is defined as the ability of a nucleic acid sequence to hybridize to a disclosed nucleic acid sequence. A nucleic acid sequence is "substantially complementary" to the dislosed nucleic acid sequence if the sequence is able to hybridize to greater than 80% of the residues, aligning the sequences and introducing gaps if necessary to achieve maximum complementarity. Preferably, a substantially complementary sequence is greater than 90%, most preferably it is greater than 95% complementary.

Cathepsin Y biological activity is defined as the sequential removal of the carboxy-terminal amino acids from a peptide without endopeptidase activity, one amino acid at a time.

The term "transformation" refers to introducing DNA into an organism or host cell so that the DNA is replicable, either as an extrachromosomal element or by chromosomal integration.

The term "transfection" refers to the introduction of DNA into a host cell. It is contemplated that coding sequences may be expressed in transfected cells. Numerous methods of transfection are known to the ordinarily skilled artisan, for example $CaPO_4$ and electroporation.

II. β-Amyloid Production Suppressors

This invention is based, in part, on the discovery of compounds that have been found to inhibit β-amyloid (βAP) secretion in cells. This invention provides methods for inhibiting βAP secretion in cells, inhibiting the deposition of plaque and treating Alzheimer's disease.

In one embodiment, this invention provides a method of inhibiting β-amyloid production in cells producing βAP, comprising administering to such cells an inhibitory amount of a compound of formula I:

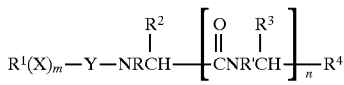

or pharmaceutically acceptable salts thereof.

In formula I, R is hydrogen, alkyl of from 1 to 6 carbon atoms or can be joined with $R^2$ to form a ring structure of from 4 to 10 carbon atoms and R' is hydrogen, alkyl of from 1 to 6 carbon atoms or can be joined with $R^3$ to form a ring structure of from 4 to 10 carbon atoms. Preferably, R and R' in formula I are hydrogen.

$R^1$ can be alkyl of from 1 to 4 carbon atoms substituted with from 1 to 5 substituents selected from the group consisting of aryl of from 6 to 10 carbon atoms, aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, cycloalkyl of from 3 to 8 carbon atoms and heterocycles of from 3 to 14 carbon atoms having from 1 to 3 heteroatoms selected from the group consisting of nitrogen, oxygen and sulfur wherein said substituted alkyl group is optionally further substituted with from 1 to 2 hydroxyl groups, alkenyl of from 2 to 4 carbon atoms substituted with from 1 to 4 substituents selected from the group consisting of aryl of from 6 to 10 carbon atoms, aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, cycloalkyl of from 3 to 8 carbon atoms and heterocycles of from 3 to 14 carbon atoms having from 1 to 3 heteroatoms selected from the group consisting of nitrogen, oxygen and sulfur, aryl of from 6 to 10 carbon atoms, aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, fluorenyl, and heterocycles of from 3 to 14 carbon atoms having from 1 to 3 heteroatoms selected from the group consisting of nitrogen, oxygen and sulfur.

Preferred values for $R^1$ include benzyl, trityl, diphenylmethyl, 4-phenylbutyl, 2-phenylethyl, naphthyl, pyridyl, fluorenyl, xanthanilyl, and the like.

$R^2$ and $R^3$ are independently side chains of a D- or L-amino acid having at least 2 carbon atoms with the proviso that $R^2$ and $R^3$ are not proline. Such side chains refer to the $R^8$ substituent found on naturally occurring and synthetic amino acids of the formula $H_2NCHR_8COOH$. Side chains of naturally occurring amino acids include, by way of example only, those where $R^8$ is the L-isomer of $(CH_3)_2CH$— (valine), $(CH_3)_2CHCH_2$— (leucine), $CH_3CH_2CH(CH_3)$— (isoleucine), $\phi CH_2$— (phenylalanine), (3— indolyl)-$CH_2$— (tryptophan), $CH_3SCH_2CH_2$— (methionine), $CH_3CH$ (OH)— (threonine), p—HO—$\phi$—$CH_2$— (tyrosine), $H_2NC$(O)$CH_2$— (asparagine), $H_2NC(O)CH_2CH_2$— (glutamine), $HOC(O)CH_2$— (aspartic acid), $HOC(O)CH_2CH_2$— (glutamic acid), $H_2NCH_2CH_2CH_2CH_2$— (lysine), $H_2NC$(NH)$NHCH_2CH_2CH_2$— (arginine), 4-imidazolyl-$CH_2$— (histidine) and the like.

Side chains of synthetic amino acids include the D-isomer of the above noted naturally occurring amino acids as well as those where $R^8$ is selected from the group consisting of alkyl of from 2 to 6 carbon atoms (where the alkyl group does not occur in naturally occurring amino acids), cycloalkyl of from 3 to 8 carbon atoms, and alkyl of from 1 to 6 carbon atoms substituted with from 1 to 2 substituents selected from the group consisting of aryl of from 6 to 10 carbon atoms, aryl of from 6 to 10 carbon atoms substituted with from 1 to 3 substituents selected from the group consisting of alkyl of from 1 to 6 carbon atoms, alkoxy of from 1 to 6 carbon atoms, aryl of from 6 to 10 carbon atoms, and aryloxy of from 6 to 10 carbon atoms, and heteroaryl of from 3 to 14 carbon atoms having from 1 to 3 heteroatoms selected from the group consisting of nitrogen, oxygen and sulfur (where the substituted alkyl group does not occur in naturally occurring amino acids).

Preferred amino acid side chains include the D- and L-isomers of valine, leucine, phenylalanine, tryptophan and isoleucine.

$R^4$ can be —C(O)CH=N=N, —$CH_2$OH, —C=NOH, and —C(O)$R^5$ where $R^5$ is hydrogen, alkyl of from 1 to 6 carbon atoms, haloalkyl of from 1 to 6 carbon atoms and 1 to 2 halo groups, alkoxy of from 1 to 6 carbon atoms, —$NR^6R^7$ where $R^6$ and $R^7$ are independently selected from the group consisting of hydrogen, alkyl of from 1 to 6 carbon atoms and aryl of from 6 to 10 carbon atoms, and —N(CH$_3$)OCH$_3$. Preferably, $R^4$ is —CH=N=N or —C(O)H.

X can be —O—, —$NR^9$— or —S— where $R^9$ is selected from the group consisting of hydrogen, alkyl of from 1 to 6 carbon atoms and aryl of from 6 to 10 carbon atoms. Preferably X is —O—.

Y can be —C(O)— or —C(S)— and is preferably —C(O)—.

m is an integer equal to zero or one and n is an integer equal to zero to two. Preferably, n is an integer equal to zero or one.

III. Synthesis of β-Amyloid Suppressors

Generally, the compounds of the invention are synthesized using standard techniques and reagents. The linkages between the various groups in these compounds comprise, for example, a carbon atom linked to a nitrogen atom of an amide, a thioamide, a carbamate, a thiocarbamate, a urea, a thiourea, etc. The methods and reagents for forming such bonds are well known and readily available. See, e.g., March, *Advanced Organic Chemistry*, 4th Ed. (Wiley 1992), Larock, *Comprehensive Organic Transformations* (VCH 1989); and Furniss, et al. and Furniss, *Vogel's Textbook of Practical Organic Chemistry* 5th ed. (Longman 1989), each of which is incorporated herein by reference. In addition, any functional groups present may require protection and deprotection at different points in the synthesis of the compounds of the invention. Such techniques are well known (see, e.g., Green and Wuts, *Protective Groups in Organic Chemistry* (Wiley 1992), also incorporated herein by reference).

The synthesis of the compounds of this invention can start with, for example, an amino acid (in the case where n is 0), a dipeptide (in the case where n is 1) or a tripeptide (in the case where n is 2).

Reaction Scheme 1 below illustrates one example of the synthesis of compounds wherein n is 1, Y=—C(O)— and $R^4$ is —C(O)H which employs as starting material a dipeptide structure. It is understood, however, that, for compounds where n is 0 or 2, similar syntheses can be used with the exception that either an amino acid is employed as the starting material (for n equal to 0) or a tripeptide is employed for n equal to 2.

As shown in Reaction Scheme 1, dipeptide 1 is reacted with at least a stoichiometric amount of $R^1(X)_mC(O)Z$, where $R^1$, X and m are defined as above and Z is suitable leaving group such as a halo group under conditions suitable to form dipeptide 2 terminally N-capped with the $R^1(X)_mC$(O)— substituent. Alternatively, $R^1(X)_mC(S)Z$ substituents can be used to prepare compounds where Y is —C(S)—.

Depending upon the reaction conditions employed, it may be necessary or desirable to protect the carboxyl group of dipeptide 1 with a conventional removable blocking group such as conversion to as an alkyl or aryl ester. Likewise, any reactive substituents found on the amino acid side chains $R^2$ and $R^3$ of dipeptide 1 will require blocking and subsequent deblocking with a conventional removable blocking group.

The reaction is conducted in the presence of a suitable inert diluent typically in the presence of a base to scavenge any acid generated during the reaction, particularly if Z is halo. Suitable inert diluents include, by way of example, methylene chloride, chloroform, toluene, pyridine, etc. Suitable bases include triethylamine, diethylisopropylamine, pyridine, and the like. The reaction is typically conducted at from about 0° C. to about 25° C. and is typically complete in from about 1 to about 12 hours. The resulting dipeptide 2 can be recovered by conventional means such as distillation, chromatography, filtration, etc. or alternatively is converted to aldehyde compound 3 without recovery and/or purification.

Dipeptide 2 is then reduced to provide the desired aldehyde 3 via conventional methods such as those described in March or Larock, supra. Such methods include, for example, direct reduction of the carboxyl group of dipeptide 2 to alcohol 4, by, e.g., reaction of the acid with di-(iso-butyl) aluminumhydride (DIBALH) (see, e.g., *J. Gen. Chem.*

USSR 34:1021 (1964)), or di-(N-methylpiperazinyl) aluminum hydride (see, e.g., *J. Org. Chem.* 49:2279 (1984)) followed by partial reoxidation to the aldehyde. See, e.g., Luly, et al., *Journal of Organic Chemistry*, 52(8):1487 et seq. (1987).

Alternatively, the aldehyde may be formed via the acid chloride using, e.g., thionyl chloride, followed by reduction using, for example, hydrogen and a palladium catalyst, tri-(t-butoxy)lithium aluminum hydride, sodium borohydride (alone or with pyridine or cadmium chloride).

Preferably, however, the carboxyl group of dipeptide 2 is first converted to the corresponding N,O-dimethylhydroxamide 5 which is then reduced by, for example, lithium aluminum hydride to provide for aldehyde 3. The N,O-dimethylhydroxamide 5 is formed, for example, by reaction of dipeptide 2 with at least a stoichiometric amount of benzotriazol-1-yloxy-tris(dimethylamino)phosphonium hexafluorophosphate (BOP) and 4-methyl morpholine in an inert diluent at a temperature of from about 10° C. to about 40° C. for a period sufficient to form the activated ester. Suitable inert diluents include, by way of example, N,N-dimethyl-formamide, pyridine, etc. The product is preferably not recovered but rather the reaction solution is used to convert the activated ester to the N,O-dimethylhydroxylamide 5.

The activated ester is converted to the N,O-dimethylhydroxylamide 5 by reaction with at least a stoichiometric amount of N,O-dimethylhydroxylamine hydrochloride at a temperature of from about 10° C. to about 40° C. for a period sufficient to form the desired N,O-dimethylhydroxylamide 5. The resulting product can be recovered by conventional methods such as chromatography, distillation, filtration, etc. or, alternatively, used directly in the next step of the synthesis which converts the N,O-dimethylhydroxylamide 5 to aldehyde 3 by conventional reduction using a suitable reducing agent such as lithium aluminum hydride.

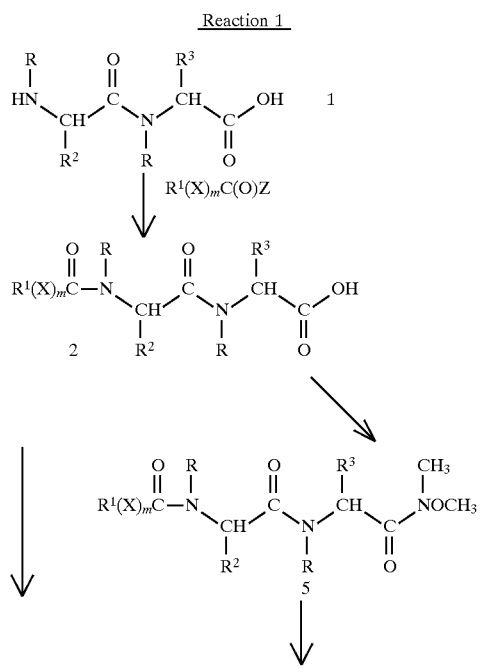

Reaction 1

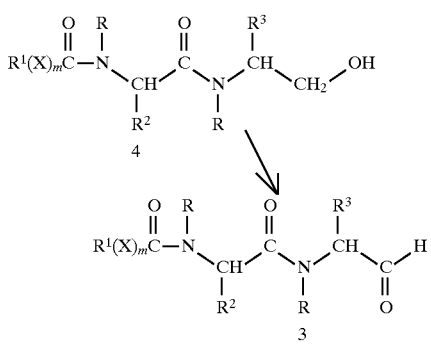

In the case of amino acids, the conversion of commercially available N-protected amino acids (n=0) to the corresponding N-protected N',O-dimethylhydroxylamide and subsequent reduction to aldehyde 3 follows the procedure set forth above. The first step in this process is illustrated in FIG. 1 and involves conversion of N-protected amino acid 6 to the corresponding N-protected N',O-dimethylhydroxylamide 7. Preferably, the N-protecting group on such amino acids is of the formula $R^1(X)_mC(O)$— such that, upon reduction, the resulting compounds are of formula I above and, in the case of FIG. 1 is illustrated as $\phi CH_2OC(O)$—. Alternatively, however, the N-protecting group can be removed by conventional methods and the resulting free amine N',O-diethylhydroxylamide 8 can be reacted with $R^1(X)_mC(O)Z$ and subsequently reduced to provide for compounds of formula I above (not shown).

The free amine N',O-dimethylhydroxylamide 8 obtained by deprotecting the N-protected N',O-dimethylhydroxylamides can also be used to form compounds of formula I where n=1 as also illustrated in FIG. 1. Specifically, in this figure, the free amine 8 is coupled to the free acid of amino acid 9 having a $R^1(X)_mC(O)$—[e.g., $\phi CH_2OC(O)$—] group attached to form dimer 10 which, upon subsequent conventional reduction with, for example, lithium aluminum hydride (LAH) forms aldehyde 11.

Conversion of the aldehydes 3 and 11 to the corresponding oximes or the corresponding diazoketones can be accomplished using chemistry known per se in the art. For example, oxime formation is accomplished via reaction of aldehydes 3 and 11 with hydroxylamine whereas diazoketones were prepared using the procedure reported by Shaw (Green, George D. J., Shaw, Elliot (1981) *J. Biol. Chem.* 256, 1923–1928.

Compounds 2 and 6 can be readily converted via art recognized methods to provide for $R^5$=alkoxy of from 1 to 6 carbon atoms and $R^5$=—$NR^6R^7$ where $R^6$ and $R^7$ are independently hydrogen, alkyl of from 1 to 6 carbon atoms or aryl of from 6 to 10 carbon atoms. Likewise, compounds 2 and 6 can be readily converted to ketones ($R^5$=alkyl of from 1 to 6 carbon atoms) via methods known per se in the art.

The starting materials employed in Reaction Scheme 1 are known in the art. For example, dipeptides 1 may be purchased commercially (e.g., from Bachem Bioscience, Inc., Philadelphia, Pa.) or synthesized from standard procedures, such as those described in *Synthetic Peptides: A User's Guide*, Grant, Ed. (Freeman, 1992), *Solid Phase Peptide Synthesis: A Practical Approach*, Atherton, et al., Eds. (Oxford 1989) or *Synthesis of Optically Active γ-Amino Acids*, Williams (Pergammon 1989). Generally, dipeptides are synthesized from amino acids which themselves are commercially available (e.g., from Bachem or Aldrich, Milwaukee, Wis.) by, for example, the methods described above or by using known methods such as the Strecker method (see, e.g., March, or Williams, supra).

Typically, the coupling of the amino acids to form dipeptide 1 requires the blocking of the α-amino moiety of the N-terminal amino acid, and any other potentially reactive groups present on the side chain, from reaction with the activated carboxyl group of the C-terminal amino acid. Conventional N-terminal amino protecting groups include, by way of example, t-butyloxycarbonyl (BOC) or benzyloxycarbonyl (Cbz).

Similarly, reagents of the formula $R^1(X)_m C(O)Z$ are also known per se in the art and some of these materials are also commercially available. For example, benzoyl chloride ($R^1$= -φ, m=0, Y=—C(O)— and Z=Cl), phenyl chloroformate ($R^1$=φ, X=O, m=1, Y=—C(O)— and Z=Cl), benzyl chloroformate ($R^1$=φ, X=O, m=1, Y=—C(O)— and Z=Cl), diphenyl acetyl chloride ($R^1$=(φ)$_2$CH—, m=0, Y=—C(O)— and Z=Cl) are all commercially available reagents as are phenyl chlorothionoformate ($R^1$=φ, m=1, X=O, Y=—C(S)— and Z=Cl) and phenyl chlorodithioformate ($R^1$=φ, m=1, X=S, Y=—C(S)— and Z=Cl).

IV. Pharmaceutical Formulations

When employed as pharmaceuticals, the compounds of formula I above are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients may be prepared as follows:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet form may be prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation may be prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, may be prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament may be made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient may be made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose may be made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules containing 15 mg of medicament may be made as follows:

| Ingredient | Quantity (mg/capsule) |
| --- | --- |
| Active Ingredient | 15.0 mg |
| Microcrystalline Cellulose | 135.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 ml |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

V. Cathepsin Y Compositions

Cathepsin Y is a novel carboxypeptidase having a molecular weight of approximately 31 kD and the amino acid sequence set forth in SEQ ID No. 3. Cathepsin Y is involved in the release of βAP from βAP-producing cells. The βAP production inhibition provided by the compounds of formula I described above appears to at least partially occur through inhibition of Cathepsin Y. Cathepsin Y is able to cleave a wide variety of carboxy-terminal amino acids, with particular activity against aliphatic carboxy-terminal amino acids. The ability of Cathepsin Y to cleave the terminal amino acid is strongly affected by the nature of the amino acid residue located two positions away from the terminal amino acid being cleaved. Such specificity is characteristic of the papain super family of cysteine proteases.

Cathepsin Y according to the present invention can be obtained from both natural and synthetic sources. Natural Cathepsin Y may be isolated and purified from a variety of mammalian cellular sources, including human 293 cells, human HS683 cells, human brain etc. Cells from these sources may be collected and disrupted to produce a lysate. Cellular and other debris from the resulting lysate may be separated, for example, by centrifugation, and the resulting supernatant subjected to a series of conventional purification steps. Specific methods for isolating and at least partially purifying Cathepsin Y from natural sources are set forth in detail in the Experimental section hereinafter. Cathepsin Y compositions of the present invention will be at least partially purified, typically being at least 10% by weight (w/w) pure and being free from contaminants and substances which would interfere with the enzymatic activity. Usually the Cathepsin Y compositions will be at least 25% w/w pure, more usually being at least 50% w/w pure, and preferably being at least 75% w/w pure, or higher. In many cases it will be desirable to obtain substantially pure (homogeneous) compositions of the Cathepsin Y of the present invention, typically being greater than 90% w/w pure, preferably being greater than 95% w/w pure and sometimes being 99% w/w pure or higher. Compositions having such high purity can be obtained using conventional protein purification techniques in conjunction with assays for the desired Cathepsin Y activity, as described in the Experimental section hereinafter.

Synthetic preparation of the Cathepsin Y compositions may be based on either the cDNA sequence (SEQ.ID No. 2) or the amino acid sequence (SEQ.ID No. 3) of the native Cathepsin Y. Cathepsin Y from other mammals, as well as allelic forms of Cathepsin Y, may be identified using degenerate oligonucleotide probes to screen suitable human and non-human libraries. Suitable libraries are available from a number of sources. cDNA libraries may be screened by a variety of conventional techniques to identify cDNAs which encode Cathepsin Y of the present invention. Such techniques include direct hybridization, polymerase chain reaction (PCR)-amplified hybridization, the use of anti-Cathepsin Y antibodies, and the like. The identification of other Cathepsin Y cDNA sequences can be confirmed by introducing the identified DNA inserts into an appropriate plasmid vector for expression in an appropriate host, with the resulting recombinant expression vector being mapped by restriction enzyme cleavage and Southern blotting. Internally consistent clones may then be sequenced, with an internally consistent sequence being confirmed for Cathepsin Y.

Purified Cathepsin Y compositions of the present invention may be natural, i.e., including the entire Cathepsin Y enzyme or fragments thereof isolated from the natural source, as described above, or may be synthetic, i.e., including the entire protein or fragment or analog thereof, prepared by the techniques described below. In the case of both the natural and synthetic Cathepsin Y, the fragments and analogs will preferably retain at least a portion of the native biological activity, i.e., usually retaining at least the native proteolytic activity.

Synthetic polypeptides representing intact Cathepsin Y or biologically active fragments or analogs thereof may be prepared by either of two general approaches. First, polypeptides may be synthesized using conventional solid-phase methods employing automated, commercial systems. The second and generally preferred method for synthesizing Cathepsin Y polypeptides according to the present invention involves the expression in cultured cells of recombinant DNA molecules encoding for the expression of all or a portion of the Cathepsin Y protein. The recombinant DNA molecule may incorporate either a natural or synthetic gene, with natural genes and cDNA being obtainable as described above. Synthetic polynucleotides may be prepared using solid phase techniques and automated commercial synthesizers. Double-stranded fragments may then be obtained either by synthesizing the complementary strand and annealing the strands together under appropriate conditions, or by adding the complementary strand using DNA polymerase with an appropriate primer sequence.

Natural or synthetic DNA fragments encoding the desired Cathepsin Y protein, fragment, or analog thereof will be incorporated in the DNA construct capable of introduction to and expression in an in vitro cell culture. Usually, the DNA constructs will be suitable for replication in a unicellular host, such as yeast or bacteria. Alternatively, the DNA constructs may be suitable for introduction into and integration within mammalian cells, preferably human cells, by a variety of now well known techniques. The expression of the Cathepsin Y protein from such constructs will be performed under conditions wherein the Cathepsin Y is expressed. It is understood that such conditions will depend on the vector and the host cell used and can be determined by a person skilled in the art in light of the circumstances.

The nucleic acid may be directly labelled with any detectable label known the art, including radioactive nuclides such as $^{32}P$, $^{3}H$ and $^{24}S$, fluorescent markers such as fluorescein, Texas Red, AMCA blue, lucifer yellow, rhodamine and the like or any cyanin dye which is detectable with visible light. The nucleic acid may be directly labelled using methods such as PCR, random priming, end labelling, nick translation and the like. Alternatively, nucleic acids may be indirectly labelled by incorporating a nucleotide covalently linked to a hapten or other molecule such as biotin or digoxigenin (Boehringer Mannheim, Indianapolis, Ind.) and performing a sandwich hybridization with a labelled antibody or other molecule directed to that hapten. For example, where biotin is incorporated into the nucleic acid avidin conjugated so a detactable label can be used.

The isolated and purified Cathepsin Y polypeptides of the present invention may be utilized as proteases in a variety of biological and chemical systems. Additionally, the Cathepsin Y polypeptides may be used in screening assays for identifying test compounds which have βAP inhibition activity. It is further contemplated that Cathepsin Y can be used diagnostically to evaluate a patient's risk for AD based on the presence and amount of this enzyme present in the patient's body fluid.

The isolated and purified nucleic acids substantially homologous to the sequence of FIGS. 4A–4E, nucleic acids substantially complementary to the sequence of FIGS. 4A–4E and fragments of the sequence of FIGS. 4A–4E can be used to probe specifically for the presence of Cathepsin Y RNA or DNA in tissues or cloned libraries. The purified nucleic acids can be used to identify those tissues or cells which express RNA encoding for Cathepsin Y. The preferred size of the nucleic acid fragments of FIGS. 4A–4E is at least 12 base pairs, preferably the fragments are at least 20 base pairs, more preferably of the fragments are at least 50 base pairs. The nucleic acid may be RNA or DNA.

VI. Screening Assays for βAP Inhibition Activity

Cathepsin Y can be used in quantitative assays for the identification of compounds having βAP-production inhibition activity based on inhibition of the carboxypeptidase activity of the Cathepsin Y. Such assays are performed by observing the ability of Cathepsin Y to cleave the carboxy-terminal residue on a suitable oligopeptide substrate. Test compounds which are able to inhibit such carboxypeptidase activity are considered candidates for further testing to determine their βAP-production inhibition activity. Those test compounds which are unable to inhibit the carboxypeptidase activity are considered less likely candidates for further testing. An exemplary assay for βAP-production inhibition activity using Cathepsin Y is described in detail in the Experimental section below.

The following synthetic and biological examples are offered to illustrate this invention and are not to be construed in any way as limiting the scope of this invention. Unless otherwise stated, all temperatures are in degrees Celsius. Also, in these examples, unless otherwise defined below, the abbreviations employed have their generally accepted meaning:

BOP Reagent=benzotriazol-1-yloxy-tris(dimethylamino) phosphonium hexafluorophosphate
bp=base pairs
CBZ=carbobenzyloxy
DTT=dithiothreitol
DMF=N,N-dimethylformamide
DMSO=dimethylsulfoxide
dNTP=deoxynucleoside triphosphate
DPDS=dipyridyldisulfide
EDTA=ethylene diamine tetraacetic acid
g=gram
HPLC=high performance liquid chromatography
LAH=lithium aluminum hydride
M=molar
MES buffer=2-[N-morpholino]ethanesulfonic acid
mg=milligram
mL=milliliter
mM=millimolar
mmol=millimol
$\mu$M=micromolar
N=Normal
ng=nanogram
pM=picomolar
psi=pounds per square inch
PVDF=polyvinylidene difluoride
RGW=reagent grade water
rpm=rotations per minute
$\mu$g=microgram
$\mu$L=miricroliters
$\mu$M=micromolar 293 cells were obtained from the American Type Culture Collection (ATCC CRL 1573).

293 751 SWE cells were obtained from K293 cells (human kidney cell line) stably transfected with the APP751 CDNA having the Swedish mutation.

Brij 35 was obtained from Boehringer Mannheim.

EXAMPLES

The syntheses outlined in General Procedures A–D are illustrated in FIG. 1 and depicts the synthesis of N-substituted dipeptide aldehydes.

General Procedure A
Synthesis of carbobenzyloxy (CBZ) protected amino N,O-Dimethylhydroxyamides, 7 (20 mmole scale)

The N,O-dimethythydroxyamides illustrated in FIG. 1 were synthesized on a 20 mmol scale according to the following general procedure. The CBZ protected amino acid 6 (20 mmol), BOP Reagent (30 mmol) and 4-methyl morpholine (100 mmol) were added to 100 mL of DMF and all were stirred under an atmosphere of nitrogen for 1 hour at ambient temperature. At this time N,O-dimethylhydroxylamine hydrochloride (24 mmol) was added and all were stirred for an additional 12 hours at ambient temperature. The reaction was poured into water (200 mL) then extracted with ethyl acetate (3×200 mL). The combined organic layers were washed with saturated aqueous citric acid (2×200 mL), saturated aqueous sodium bicarbonate (2×200 mL), and brine (1×300 mL). The organic layer was dried using $MgSO_4$, filtered, and concentrated to yield the desired CBZ protected N,O-dimethylhydroxylamide 7. When necessary the product was chromatographed using 50% ethyl acetate/hexanes. Purified yields were typically 70%–85%.

General Procedure B
Synthesis of amino-N,O-Dimethylhydroxyamides 8

The removal of the CBZ protecting group on the CBZ protected N,O-dimethylhydroxylamide 7 was done on a 15 mmol scale according to the following general procedure to provide for the title compound. The CBZ protected amino acid (15 mmol) was suspended in ethanol (20 mL) in a parr bottle. To this was added 10 weight percent of palladium on activated carbon (10% palladium). This mixture was subjected to 50 psi of hydrogen for 3 hours on a parr shaker. The solution was then degassed, filtered through a pad of celite, then concentrated to afford the desired amino N,O-dimethylhydroxyamide 8 (yields typically 60%–68%). This isolated material was used without further purification.

General Procedure C
Synthesis of CBZ protected dipeptide N,O-Dimethylhydroxyamides 10

This coupling was done on a 15 mmol scale according to the following general procedure to provide for the title compound. The CBZ protected amino acid 9 (15 mmol), BOP Reagent (22.5 mmol) and 4methyl morpholine (75 mmol) were added to 75 mL of DMF and all was stirred under an atmosphere of nitrogen for 1 hour at ambient temperature. At this time, the N,O-dimethylhydroxylamide 8 (15 mmol) was added and all was stirred for an additional 12 hours at ambient temperature. The reaction was poured into water (150 mL) then extracted with ethyl acetate (3×150 mL). The organic layers were combined and washed with saturated aqueous citric acid (2×150 mL), saturated aqueous sodium bicarbonate (2×200 mL), and brine (1×225 mL). The organic layer was dried using $MgSO_4$, filtered, and concentrated to yield the desired CBZ protected dipeptide N,O-dimethylhydroxyamide 10. When necessary, the crude product was chromatographed using 50% ethyl acetate/hexanes. Purified yields were typically 67%–81%.

General Procedure D
Synthesis of CBZ protected dipeptide aldehydes 11

The reduction of N,O-dimethylhydroxyamide 10 was done on a 10 mmol scale according to the following general procedure to provide for the title compound. The N,O-Dimethylhydroxyamide 10 (10 mmol) was suspended in diethyl ether (65 mL) and cooled to 0° C. under an atmosphere of nitrogen. To this vigorously stirred solution was added LAH (40–75 mmol), and the suspension was stirred for 1 hour at 0° C., then 1 hour at ambient temperature. The reaction was quenched with 10% aqueous citric acid (30 mL) and stirred for an additional 30 minutes. This was washed with diethyl ether (3×50 mL). The combined organic layers were washed with saturated aqueous sodium bicarbonate (1×50 mL), water (1×50 mL), brine (1×50 mL), dried over $MgSO_4$, filtered, and concentrated to yield crude aldehyde. Chromatography with 50% ethyl acetate/hexanes yielded the desired purified aldehyde 11. Purified yields were typically 45%–75%.

Figure 2:
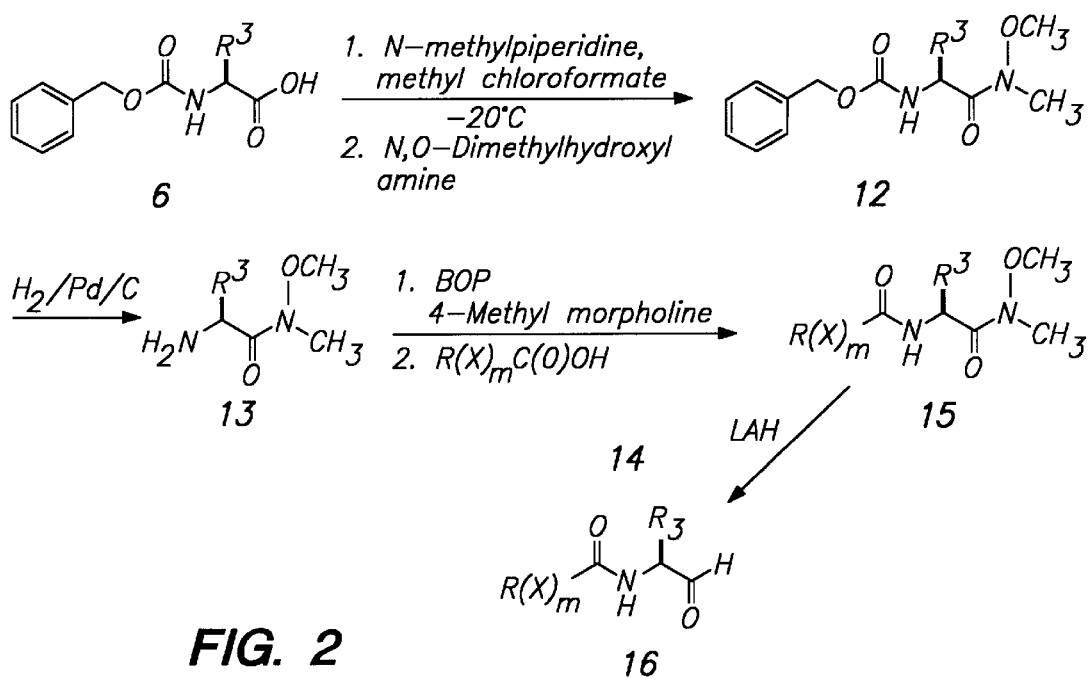

The syntheses outlined in General Procedures E–G are illustrated in FIG. 2 and depicts the syntheses of N-substituted amino acid aldehydes.

General Procedure E
Synthesis of carbobenzyloxy (CBZ) protected amino N,O-Dimethylhydroxyamides 12 (+50 mmol scale)

The N,O-dimethylhydroxyamides synthesized on a +50 mmol scale were prepared according to the following general procedure to provide for the title compound. The CBZ protected amino acid 6 (50 mmol) was added to a 2:1 methylene chloride/tetrahydrofuran solution (500 mL) and all was cooled to −20° C. under an atmosphere of nitrogen. N-methylpiperidine (52.5 mmol) was added followed by the dropwise addition of methylchloroformate (52.5 mmol). After 10 minutes, a solution of N,O-dimethylhydroxylamine (75 mmol, freebased with 75 mmol of N-methylpiperidine) in methylene chloride (50 mL) was added dropwise at a rate to maintain the internal temperature of the reaction at −20° C. After the addition was complete, the reaction was allowed to warm to ambient temperature and stirred for 3 hours. The reaction was washed with 0.2N HCl (3×125 mL), 0.2N $NaHCO_3$ (1×125 mL), water (1×125 mL), dried over $MgSO_4$, filtered and concentrated to yield the desired CBZ protected N,O-dimethyl-hydroxylamide 12 (yields were typically 80%–90%). This material was very pure and was used without further purification.

General Procedure F
Synthesis of amino-N,O-Dimethylhydroxyamides 13

The removal of the CBZ protecting group was done on a 15 mmol scale according to the following general procedure to provide for the title compound. The CBZ protected amino acid 12 (15 mmol) was suspended in ethanol (20 mL) in a parr bottle. To this was added 10 weight percent of palladium on activated carbon (10% palladium). This mixture was subjected to 50 psi of hydrogen for 3 hours on a parr shaker. The solution was then degassed, filtered through a pad of celite, then concentrated to afford the desired the desired amino N,O-dimethylhydroxyamide 13 (yields were

General Procedure G
Synthesis of amino substituted N,O-Dimethylhydroxyamides 15

This coupling was done on a 2.6 mmol scale according to the following general procedure to provide for the title compound. The carboxylic acid 14 (2.9 mmoles) BOP Reagent (2.9 mmol) and 4-methyl morpholine (10.4 imnol) were added to 35 mL of DMF and all was stirred under an atmosphere of nitrogen for 1 hour at ambient temperature. At this time the N,O-dimethylhydroxylamide 9, (2.6 mmol) dissolved in methylene chloride (5 mL) was added and all was stirred under nitrogen for 12 hours at ambient temperature. The reaction was poured into water (50 mL) then extracted with ethyl acetate (3×50 mL). The organic layers were combined and washed with saturated 0.2N aqueous HCl (2×100 mL), saturated aqueous sodium bicarbonate (133 200 mL), and brine (1×200 mL). The organic layer was dried using $MgSO_4$, filtered, and concentrated to yield the desired N-substituted N,O dimethylhydroxyamide 15. When necessary, the crude product was chromatographed using 50% ethyl acetate/hexanes. Purified yields were typically 60%–90%.

General Procedure H
Synthesis of amino substituted aldehydes 16

The reduction of the N,O-dimethylhydroxyarnide was done on a 0.5 mmol scale according to the following general procedure to provide for the title compound. N,O-Dimethylhydroxyamide 15 (0.5 mmol) was suspended in tetra-hydrofuran (30 mL) and cooled to 0° C. under an atmosphere of nitrogen. To this vigorously stirred solution, LAH (1.3 mmol) was added portion wise over a 30 minute period. Diethyl ether (60 mL) was then added followed by ice-cold 10% aqueous citric acid (80 mmol). After 30 minutes of vigorous stirring the reaction mixture was extracted with diethyl ether (5×20 mL). The combined organic portions were washed with saturated aqueous sodium bicarbonate (1×50 mL), water (1×50 mL), brine (1×50 mL), dried over $MgSO_4$, filtered, and concentrated to yield crude aldehyde. Chromatography with 50% ethyl acetate/hexanes yielded the desired purified aldehyde 16. Purified yields were typically 31%–65%.

General Procedure I
Preparation of Diazoketones

Diazoketones were prepared according to the procedure set forth by Green et al., J. Biol. Chem., "Peptidyl Diazomethyl Ketones are Specific Inactivators of Thiol Proteinases", 256(4):1923–1928 (1981). Specifically, diazomethane was freshly prepared by the slow portion wise addition of 1-methy-3-nitro-1-nitrosoguanidine (17 mmol) into a solution of diethyl ether (50 mL) that contains a 40% aqueous KOH (15 mL) at 5° C. After allowing the solution to stand for 10 minutes the diethyl ether was decanted off and dried over KOH pellets. The protected amino acid or dipeptide (5.0 mmol) and N-methyl morpholine (5.0 mmol) were added to THF (25 mL) and all was cooled to -10° C. Isobutylchioroformate (5.0 mmol) was added dropwise and the solution was stirred for an additional 5 minutes. The reaction was filtered then added dropwise to the freshly prepared solution of diazomethane (as above). All were allowed to sit undisturbed for 1 hour at 0° C. then overnight at room temperature. The diethyl ether was washed with water (3×40 mL) then brine (40 mL), dried over $MgSO_4$ and concentrated to yield the desired diazoketone. Yields were typically between 55–72%.

General Procedure J
Preparation of Alcohols

C-terminal alcohols were prepared from the corresponding C-terminal aldehydes by conventional reduction with LAH. For example, the aldehyde is combined with LAH (about 4 equivalents) in THF at approximately 0° C. Diethyl ether is then added followed by ice-cold 10% aqueous citric acid. After 30 minutes of vigorous stirring the reaction mixture is extracted with diethyl ether. The combined organic portions are washed with saturated aqueous sodium bicarbonate, water, brine, dried over $MgSO_4$, filtered, and concentrated to yield crude alcohol. Chromatography with 50% ethyl acetate/hexanes yields the desired purified alcohol.

General Procedure K
Preparation of Esters

C-terminal esters were prepared from the corresponding C-terminal carboxyl groups via conventional esterification conditions.

General Procedure L
Preparation of Amides

C-terminal amides were prepared from the corresponding C-terminal carboxyl groups or C-terminal esters via conventional amidation conditions. For example, the N-protected amino acid (20 mmol), BOP Reagent (30 mmol) and 4-methyl morpholine (100 mmol) are added to 100 mL of DMF and all was stirred under an atmosphere of nitrogen for 1 hour at ambient temperature. At this time, 1 equivalent of amine (e.g., ethyl methylamine) is added to the reaction mixture and stirred at ambient temperature until reaction completion (e.g., 12 hours).

Examples 1–80
Synthesis of Compounds of Formula I

Following General Procedures A–L, the Compounds 1–75 (Ex. 1–75) as found in Table I below were prepared. Additionally, Compounds 76–80 (Ex. 76–80) found in Table II were purchased from commercial vendors.

TABLE I $$R^1(X)_m-Y-NHCH\begin{matrix}R^2\\|\\\phantom{x}\end{matrix}\left[\begin{matrix}O&R^3\\\|&|\\CNHCH\end{matrix}\right]_n R^4 \quad I$$

| R¹ | X | m | Y | R² | n | R³ | R⁴ | R² isomer | R³ isomer | Ex. No. |
|---|---|---|---|---|---|---|---|---|---|---|
| φ-CH₂- | O | 1 | -C(O)- | -CH(CH₃)₂ | 1 | -CH₂-φ | -C(O)CH=N=N | L | L | 1 |
| φ₂CH- | — | 0 | -C(O)- | -CH₂-cyclohexyl | 0 | — | -C(O)H | L | — | 2 |
| (φ)₂-CH- | — | 0 | -C(O)- | -CH₂-φ | 0 | — | -C(O)H | L | — | 3 |
| φ-(CH₂)₄- | — | 0 | -C(O)- | -CH₂-φ | 0 | — | -C(O)H | L | — | 4 |
| (φ)₃-C- | — | 0 | -C(O)- | -CH₂-φ | 0 | — | -C(O)H | L | — | 5 |
| (φ)₂CH- | — | 0 | -C(O)- | -CH₂CH₂-φ | 0 | — | -C(O)H | L | — | 6 |
| φCH=C(φ)- | — | 0 | -C(O)- | -CH₂-φ | 0 | — | -C(O)H | L | — | 7 |
| (φ)₂-CH- | — | 0 | -C(O)- | -CH₂-(3-indolyl) | 0 | — | -C(O)H | L | — | 8 |
| φ-CH₂- | O | 1 | -C(O)- | -CH₂φ | 1 | -CH₂CH(CH₃)₂ | -C(O)H | D | L | 9 |
| φ-CH₂- | O | 1 | -C(O)- | -CH(CH₃)₂ | 1 | -CH₂CH(CH₃)₂ | -C(O)H | L | L | 10 |
| (φ)₂-CH- | — | 0 | -C(O)- | -CH₂-(2-naphthyl) | 0 | — | -C(O)H | L | — | 11 |
| φCH₂CH-<br>\|<br>φ | — | 0 | -C(O)- | -CH₂φ | 0 | — | -C(O)H | L | — | 12 |
| φCH₂- | O | 1 | -C(O)- | -CH(CH₃)₂ | 1 | -CH₂φ | -C(O)H | L | L | 13 |
| φCH₂- | O | 1 | -C(O)- | -CH₂CH(CH₃)₂ | 1 | -CH₂φ | -C(O)H | L | D | 14 |
| φCH₂- | O | 1 | -C(O)- | -CH(CH₃)₂ | 1 | -CH₂φ | -C(O)H | L | L | 15 |
| φCH₂- | O | 1 | -C(O)- | -CH(CH₃)₂ | 1 | -CH₂φ | -C(O)H | L | D | 16 |
| 2-naphthyl | — | 0 | -C(O)- | -CH(CH₃)₂ | 1 | -CH₂φ | -C(O)NOCH₃<br>\|<br>CH₃ | L | L | 17 |
| 2-quinolinyl | — | 0 | -C(O)- | -CH(CH₃)₂ | 1 | -CH₂φ | -C(O)NOCH₃<br>\|<br>CH₃ | L | L | 18 |
| 1-naphthyl | — | 0 | -C(O)- | -CH(CH₃)₂ | 1 | -CH₂φ | -C(O)H | L | L | 19 |
| 2-naphthyl | — | 0 | -C(O)- | -CH(CH₃)₂ | 1 | -CH₂φ | -C(O)H | L | L | 20 |
| 2-quinolinyl | — | 0 | -C(O)- | -CH(CH₃)₂ | 1 | -CH₂φ | -C(O)H | L | L | 21 |
| φCH₂- | O | 1 | -C(O)- | -CH(CH₃)₂ | 1 | -CH(CH₃)₂ | -C(O)H | L | L | 22 |
| φCH₂- | O | 1 | -C(O)- | -CH(CH₃)₂ | 1 | -CH₂φ | -C(O)NOCH₃<br>\|<br>CH₃ | L | L | 23 |
| φCH₂- | O | 1 | -C(O)- | -CH(CH₃)₂ | 1 | -CH₂φ | -C(O)H | D | L | 24 |
| φCH₂- | O | 1 | -C(O)- | -CH₂φ | 1 | -CH(CH₃)₂ | -C(O)H | L | L | 25 |
| φCH₂- | O | 1 | -C(O)- | -CH(CH₃)₂ | 1 | -CH₂φ | -CH₂OH | L | L | 26 |
| φCH₂- | O | 1 | -C(O)- | -CH₂CH(CH₃)₂ | 1 | -CH₂φ | -C(O)NOCH₃<br>\|<br>CH₃ | L | D | 27 |
| φCH₂- | O | 1 | -C(O)- | -CH(CH₃)₂ | 1 | -CH₂φ | -C(O)NOCH₃<br>\|<br>CH₃ | L | D | 28 |
| φCH₂- | O | 1 | -C(O)- | -CH(CH₃)₂ | 1 | -CH₂φ | -C(O)NOCH₃<br>\|<br>CH₃ | D | D | 29 |
| φCH₂- | O | 1 | -C(O)- | -CH(CH₃)₂ | 1 | -CH₂φ | -C(O)H | D | D | 30 |
| φCH₂- | O | 1 | -C(O)- | -CH₂CH(CH₃)₂ | 1 | -CH₂CH(CH₃)₂ | -C(O)NOCH₃<br>\|<br>CH₃ | L | L | 31 |
| φCH₂- | O | 1 | -C(O)- | -CH₂φ | 1 | -CH₂CH(CH₃)₂ | -C(O)NOCH₃<br>\|<br>CH₃ | D | L | 32 |
| φCH₂- | O | 1 | -C(O)- | -CH(CH₃)₂ | 1 | -CH₂CH(CH₃)₂ | -C(O)NOCH₃<br>\|<br>CH₃ | L | L | 33 |
| φCH₂- | O | 1 | -C(O)- | -CH₂φ | 1 | -CH(CH₃)₂ | -C(O)C=N=N | D | D | 34 |
| φCH₂- | O | 1 | -C(O)- | -CH₂φ | 1 | -CH₂φ | -C(O)C=N=N | L | L | 35 |

TABLE I-continued $$R^1(X)_m-Y-NHCH\underset{R^2}{|}-\left[\underset{\underset{R^3}{|}}{\overset{\overset{O}{||}}{C}NHCH}\right]_n-R^4 \quad I$$

| $R^1$ | X | m | Y | $R^2$ | n | $R^3$ | $R^4$ | $R^2$ isomer | $R^3$ isomer | Ex. No. |
|---|---|---|---|---|---|---|---|---|---|---|
| φCH₂— | O | 1 | —C(O)— | —CH(CH₃)₂ | 1 | —CH₂CH₂φ | —C(O)NOCH₃<br>\|<br>CH₃ | D | L | 36 |
| φCH₂— | O | 1 | —C(O)— | —CH(CH₃)₂ | 1 | —CH₂CH₂φ | —C(O)H | L | L | 37 |
| φCH=C(φ)- | — | 0 | —C(O)— | —CH₂-(3-indolyl) | 0 | — | —C(O)NOCH₃<br>\|<br>CH₃ | L | — | 38 |
| φCH₂- | O | 1 | —C(O)— | —CH₂φ | 0 | — | —C(O)H | L | — | 39 |
| (φ)₂CH— | — | 0 | —C(O)— | —CH₂φ | 0 | — | —C(O)NOCH₃<br>\|<br>CH₃ | L | — | 40 |
| φ(CH₂)₄— | — | 0 | —C(O)— | —CH₂φ | 0 | — | —C(O)NOCH₃<br>\|<br>CH₃ | L | — | 41 |
| φCH=C(φ)- | — | 0 | —C(O)— | —CH₂φ | 0 | — | —C(O)OCH₂φ | L | — | 42 |
| φCH₂CH(φ)- | — | 0 | —C(O)— | —CH₂-(3-indolyl) | 0 | — | —C(O)NOCH₃<br>\|<br>CH₃ | L | — | 43 |
| (φ)₂C(OH)— | — | 0 | —C(O)— | —CH₂-(3-indolyl) | 0 | — | —C(O)NOCH₃<br>\|<br>CH₃ | L | — | 44 |
| φ₂CH— | — | 0 | —C(O)— | -(p-benzyloxy) benzyl | 0 | — | —C(O)H | L | — | 45 |
| φCH₂— | O | 1 | —C(O)— | —CH(CH₃)₂ | 1 | —(CH₂)₂SCH₃ | —C(O)NOCH₃<br>\|<br>CH₃ | L | L | 46 |
| φCH₂— | O | 1 | —C(O)— | —CH(CH₃)₂ | 1 | —(CH₂)₂SCH₃ | —C(O)H | L | L | 47 |
| φCH₂CH₂— | — | 0 | —C(O)— | —CH₂φ | 0 | — | —C(O)NOCH₃<br>\|<br>CH₃ | L | — | 48 |
| (φ)₃C— | — | 0 | —C(O)— | —CH₂φ | 0 | — | —C(O)NOCH₃<br>\|<br>CH₃ | L | — | 49 |
| (φ)₂CH— | — | 0 | —C(O)— | —CH₂CH₂φ | 0 | — | —C(O)NOCH₃<br>\|<br>CH₃ | L | — | 50 |
| φ(CH₂)₄— | — | 0 | —C(O)— | —CH₂CH₂φ | 0 | — | —C(O)NOCH₃<br>\|<br>CH₃ | L | — | 51 |
| φ(CH₂)₄— | — | 0 | —C(O)— | —CH₂CH₂φ | 0 | — | —C(O)H | L | — | 52 |
| φCH—<br>\|<br>cyclohexyl | — | 0 | —C(O)— | —CH₂φ | 0 | — | —C(O)NOCH₃<br>\|<br>CH₃ | L | — | 53 |
| φCH₂CH₂— | — | 0 | —C(O)— | —CH₂φ | 0 | — | —C(O)H | L | — | 54 |
| φCH—<br>\|<br>cyclohexyl | — | 0 | —C(O)— | —CH₂φ | 0 | — | —C(O)H | L | — | 55 |
| φCH=C(φ)- | — | 0 | —C(O)— | —CH₂φ | 0 | — | —C(O)NOCH₃<br>\|<br>CH₃ | L | — | 56 |
| φCH₂— | — | 0 | —C(O)— | —CH₂φ | 0 | — | —C(O)NOCH₃<br>\|<br>CH₃ | L | — | 57 |

TABLE I-continued $$R^1(X)_m-Y-NHCH(R^2)-[C(O)NHCH(R^3)]_n-R^4 \quad I$$

| R¹ | X | m | Y | R² | n | R³ | R⁴ | R² isomer | R³ isomer | Ex. No. |
|---|---|---|---|---|---|---|---|---|---|---|
| φCH₂CH(φ)- | — | 0 | —C(O)— | —CH₂φ | 0 | — | φCH— <br> \| <br> cyclohexyl | L | — | 58 |
| φCH₂— | — | 0 | —C(O)— | —CH₂φ | 0 | — | —C(O)H | L | — | 59 |
| φCH₂CH(φ)- | — | 0 | —C(O)— | —CH₂φ | 0 | — | —C(O)NOCH₃ <br> \| <br> CH₃ | L | — | 60 |
| (φ)₂CH— | — | 0 | —C(O)— | —CH₂-(3-indolyl) | 0 | — | —C(O)NOCH₃ <br> \| <br> CH₃ | L | — | 61 |
| 9-xanthanilyl | — | 0 | —C(O)— | —CH₂φ | 0 | — | —C(O)NOCH₃ <br> \| <br> CH₃ | L | — | 62 |
| 9-fluorenyl | — | 0 | —C(O)— | —CH₂φ | 0 | — | —C(O)NOCH₃ <br> \| <br> CH₃ | L | — | 63 |
| 9-xanthanilyl | — | 0 | —C(O)— | —CH₂φ | 0 | — | —C(O)H | L | — | 64 |
| 9-fluorenyl | — | 0 | —C(O)— | —CH₂φ | 0 | — | —C(O)H | L | — | 65 |
| o-phenoxy-phenyl | — | 0 | —C(O)— | —CH₂-(3-indolyl) | 0 | — | —C(O)NOCH₃ <br> \| <br> CH₃ | L | — | 66 |
| φCH— <br> \| <br> cyclohexyl | — | 0 | —C(O)— | —CH₂-(3-indolyl) | 0 | — | —C(O)NOCH₃ <br> \| <br> CH₃ | L | — | 67 |
| φCH— <br> \| <br> cyclohexyl | — | 0 | —C(O)— | —CH₂-(3-indolyl) | 0 | — | —C(O)H | L | — | 68 |
| (φ)₂CH— | — | 0 | —C(O)— | —CH₂-cyclohexyl | 0 | — | —C(O)NOCH₃ <br> \| <br> CH₃ | L | — | 69 |
| (φ)₂CH— | — | 0 | —C(O)— | —CH₂-2-naphthyl | 0 | — | —C(O)NOCH₃ <br> \| <br> CH₃ | L | — | 70 |
| o-phenoxy-phenyl | — | 0 | —C(O)— | —CH₂φ | 0 | — | —C(O)H | L | — | 71 |
| (φ-p-OH) <br> \| <br> CH₃CH(CH₂)₂— <br> \| <br> (φ-p-OH) | — | 0 | —C(O)— | —CH₂φ | 0 | — | —C(O)H | L | — | 72 |

TABLE II

| Compound | Example No. |
|---|---|
| (structure) | 73 |
| (structure) | 74 |
| (structure) | 75 |
| (structure) | 76 |
| (structure) | 77 |

TABLE II-continued

| Compound | Example No. |
|---|---|
| (structure) | 78 |
| (structure) | 79 |
| (structure) | 80 |

General Procedure J

Cellular Screen for the Detection of Inhibitors of β-Amyloid Production

Compounds of this invention were assayed for their ability to inhibit β-amyloid production in a cell line possessing the Swedish mutation (293 751 SWE cells). This screening assay employed 293 751 SWE cells which were derived from K293 cells (human kidney cell line) which were stably transfected with the gene for amyloid precursor protein 751 (APP751) containing the double mutation $Lys_{652}Met_{652}$ to $Asn_{651}Leu_{652}$ (APP751 numbering) in the manner described by Schenk, et al., International Patent Application Publication No. 94/10569, "*Methods and Compositions for the Detection of Soluble β-Amyloid Peptide*", published 11 May 1994 and Citron, et al., Nature, 360:672–674 (1992) the disclosures of which are incorporated herein by reference in their entirety. This mutation is commonly called the Swedish mutation and the cells, designated as "293 751 SWE", were plated in Corning 96-well plates at $1.5–2.5 \times 10^4$ cells per well in Dulbecco's minimal essential media plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a peptide, dipeptide or tripeptide described herein (drug) containing media per well for a two hour pretreatment period and cells were incubated as above. Drug stocks were prepared in 100% dimethylsulfoxide such that at the final drug concentration used in the treatment, the concentration of dimethylsulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR centrifuge at 1200 rpm for five minutes at room temperature to pellet cellular debris from the conditioned media. From each well, 100 μL of conditioned media or appropriate dilutions thereof were transferred into an ELISA plate precoated with antibody 266 against amino acids 13–28 of β-amyloid peptide as described by Schenk, et al. in International Patent Application Publication No. 94/10569 supra. and stored at 4° C. overnight. An ELISA assay employing labelled antibody 6C6 against amino acids 1–16 of β-amyloid peptide was run the next day to measure the amount of β-amyloid peptide produced.

Cytotoxic effects of the compounds were measured by a modification of the method of Hansen, et al., J. Immun. Meth., 119:203–210 (1989) which is incorporated herein by reference in its entirety. To the cells remaining in the tissue culture plate was added 25 μL of a 3,(4,5-dimethylthiazol-2-yl)2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that, among others, the compounds of Examples 1–80 each were able to reduce β-amyloid peptide production as compared to control.

Moreover, these compounds did not have a significant cytotoxic effect on the 293 751 SWE cells.

Thus, the compounds of this invention are useful for reducing β-amyloid peptide production in cells and, accordingly, would be useful in treating humans in vivo for AD.

Summary of Cathepsin Y (31 kD) Purification and Characterization

The strong inhibition of βAP release observed with the peptide (and non-peptide) aldehydes suggested the existence of a specific protease which is the target for these inhibitors. In order to isolate such an enzyme, an affinity matrix was constructed using a modified version of the prototype aldehyde inhibitor. The compound $NH_2$-Val-Phe-semicarbazone was synthesized, then coupled to an epoxy Sepharose® matrix as described below, following which the sernicarbazone functionality was chemically converted to the aldehyde.

The binding of an active protease to the aldehyde column involves the equilibrium formation of a reversible covalent bond, between the active site cysteine residue of the protease with the aldehyde or other equivalent functionality. Elution of the protease in this case was achieved by using DPDS, which forms a disulfide linkage with the active site cysteine, and thus displaces the enzyme from the column. Recovery of enzymatic activity following elution is achieved by incubating in an excess of reducing agents such as β-mercaptoethanol or dithiothreitol.

Figures 3A, 3B:
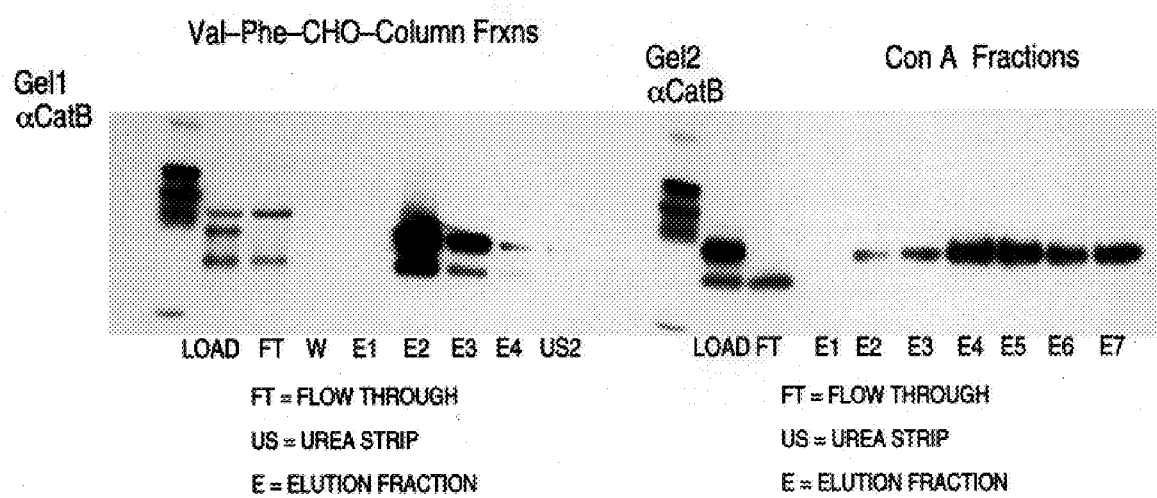
FIGS. 3A–3C illustrate typical purification profiles, analyzed by Western blotting, of Cathepsin Y.
Figure 3C:
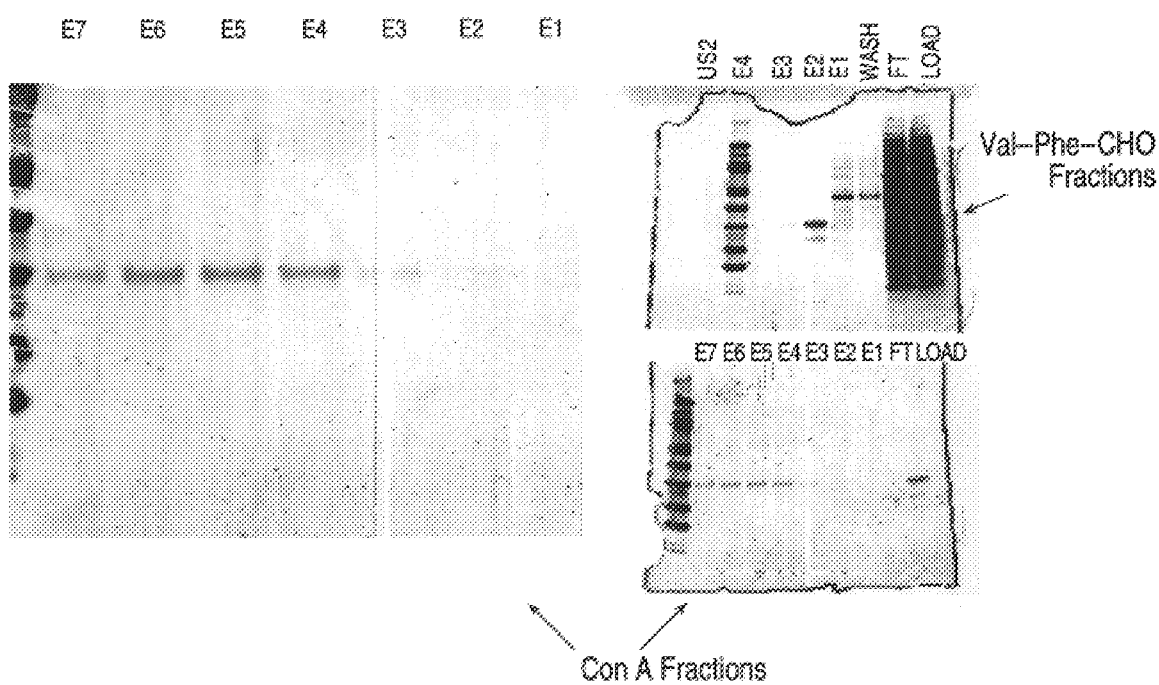
Figure 4A:
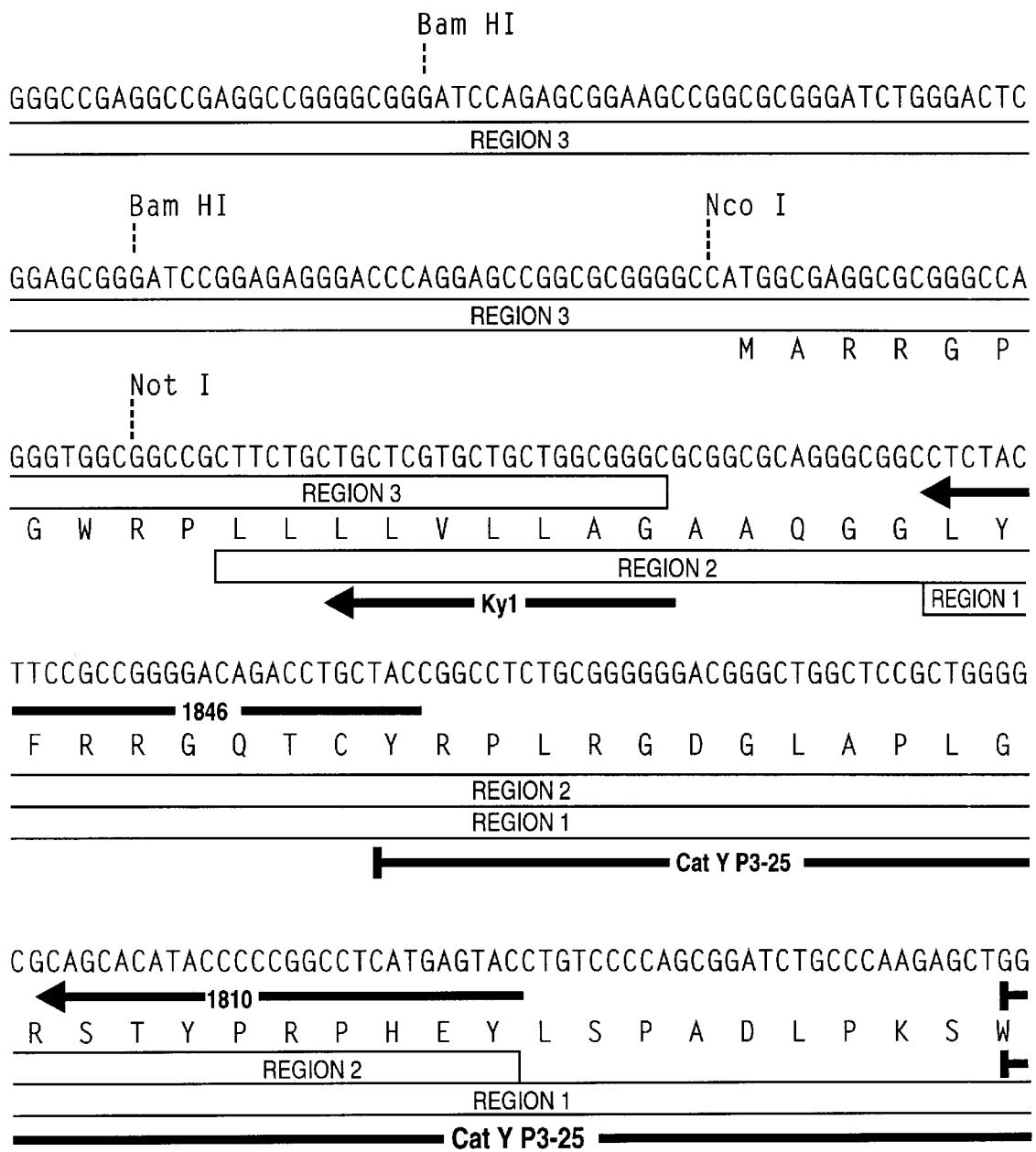
Figure 4B:
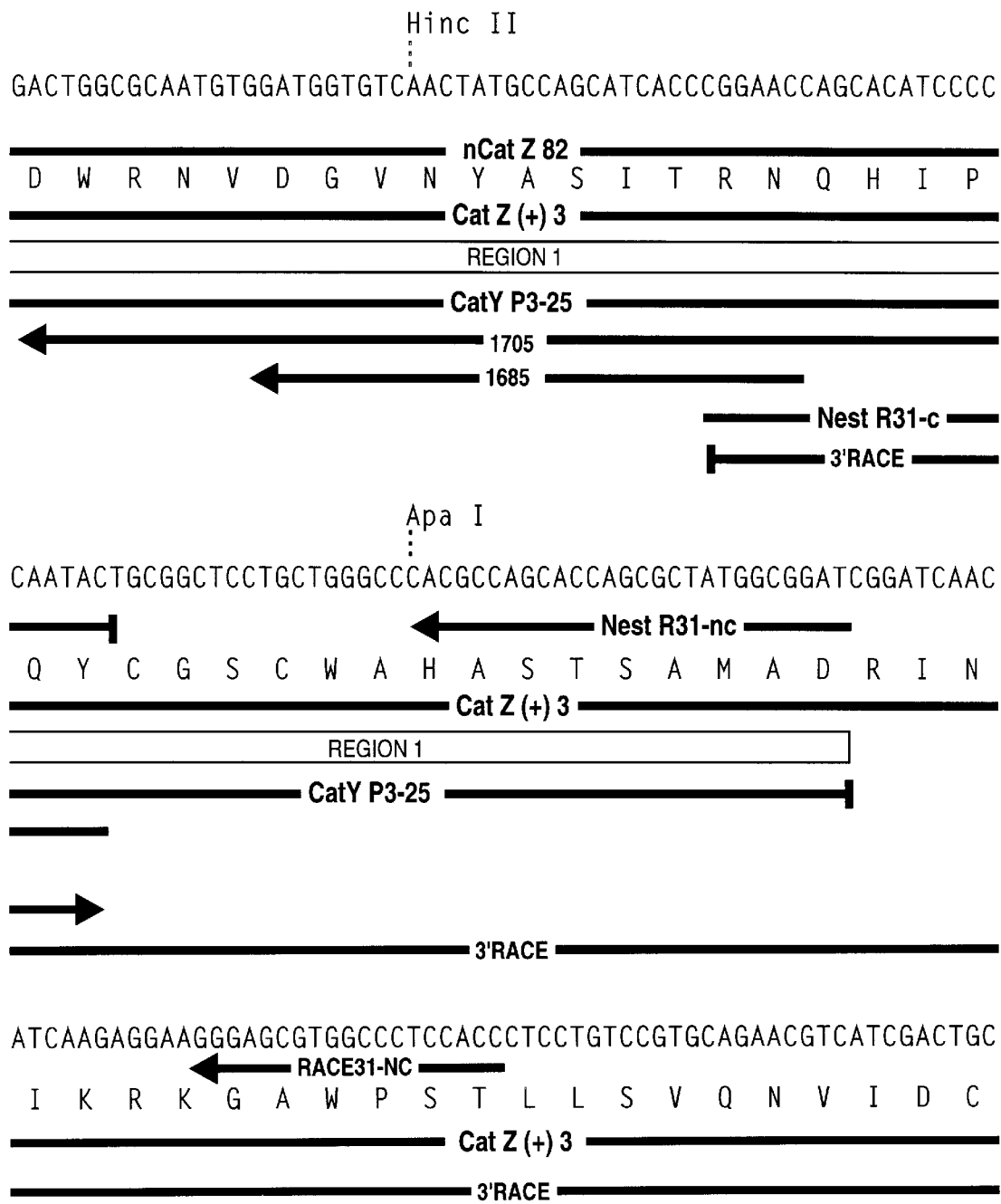

The identification of Cathepsin Y was facilitated by the serendipitous observation that a polyclonal antibody to human Cathepsin B ("anti-cat B") recognized an approximately 31 kD band as the most strongly reactive band recognized on a Western blot of fractions eluted from the aldehyde affinity matrix. FIGS. 3A–3C show a typical purification profile, analyzed by both Western blotting with the anti-cat B as well as protein staining of the purified fractions. The Western blot of fractions from the affinity matrix (FIG. 3A) shows that the anti-cat B antibody reacts strongly with three major bands in the soluble cell extract ("load"), of which the middle band (approximately 31 kD) binds most strongly to the matrix, being essentially quantitatively depleted in the flow through ("FT"). Elution with the DPDS results in the recovery of both the 31 kD band as well as the partly bound lower MW (cellular Cathepsin B). The 31 kD band is then purified away from the contaminating Cathepsin B using a concanavalin A column, which results in the selective binding and subsequent elution of the 31 kD protein band (FIG. 3B). Analysis of the fractions eluted from the concanavalin A column by Coomassie blue revealed a single protein band co-migrating exactly with the Western blot reactivity (FIG. 3C).

Preparation of ValPhe-aldehyde affinity matrix 3.2 gm of Epoxy Sepharose® (Pharmacia) was swelled in 50 mL of reagent grade distilled water (RGW) for at least 20 minutes at room temperature, and washed on a coarse Buchner filter funnel with one liter of RGW. At no stage in any of the washes was the resin cake allowed to go to complete dryness. 4.2 mL of 0.2M sodium borate, pH 9.5, was added to 1.05 mL of 25 mg/mL valylphenylalanylsemicarbazone (ValPheSC), and the washed Epoxy Sepharose was added to the resulting solution. The suspension was incubated with rotation at 37° C. for 24–26 hours. The Sepharose was sedimented by centrifugation at 550 rpm in a GSR rotor for 5 minutes, then resuspended in 40 mL of 1.0M ethanolamine, pH 8.2, and incubated as before overnight (16–18 hours). The coupled Sepharose (ValPheSC-Sepharose) was washed on a coarse Buchner filter funnel with 350 mL of 33% DMSO, then with 350 mL of RGW. The semicarbazone was converted to the corresponding aldehyde by incubation in 80 mL of methanol:acetic acid-:formaldehyde (5:1:1) at room temperature, with rotation, overnight. The Sepharose was sedimented by centrifugation as above, and incubated with fresh methanol:acetic acid-:formaldehyde as above, for 10 hours. The ValPhe-Sepharose was washed as above with 600 mL of RGW, and stored at 4° C. as a 50% slurry in 0.05% sodium azide.

Preparation of Cathepsin Y

All operations, unless noted, were performed at 4° C. or on ice. Frozen, pelleted wild-type derived 293 cells were thawed and resuspended in 5 volumes of MES buffer (20 mM MES, 2 mM EDTA, 0.1% Brij 35, pH 6.0). The suspension was homogenized for 30 seconds using either a Brinkman PT 1200 or a Tissue Tearor 985-370. The homogenate was centrifuged at 15,000 rpm (31,000×g) for 20 minutes. The supernate was collected, received 5 mM DTT, and was applied to a ValPhe column containing the ValPhe aldehyde prepared as above. The column was pre-equilibrated with MES buffer containing 0.1M NaCl.

Typically, 20 mL of 293 cell supernate was applied to a 1.0 mL column, although over 60 mL of supernate per mL of column can be applied without saturation of the column. The column was washed with one bed volume of 0.1M NaCl in MES buffer, then with 10 bed volumes of 0.2 mL NaCl in MES buffer, followed by 10 more bed volumes of 0.1M NaCl-MES buffer. The column received 0.75 volumes of 2 mM dipyridyldisulfide (DPDS) in 20 mM sodium acetate, pH 4.5, and was plugged and stored overnight. The column then received 1.25 volumes of the DPDS solution; the fraction collected at this point contained the bulk of the eluted Cathepsin Y and B. The column was eluted with at least 3 more volumes of DPDS solution, followed by 5 volumes of 6M urea. Fractions of one column volume were collected.

The peak of the DPDS eluted material received 0.1M NaCl, 1 mM $MnCl_2$, and 1 mM $CaCl_2$, and was applied to a 1.0 mL column of Concanavalin A-agarose equilibrated with wash buffer (0.1M NaCl, 50 mM NES, 1 mM $MnCl_2$, mM $CaCl_2$, pH 6.0). After the starting material had been applied, the column was washed with 5 mL of wash buffer, followed by 1 mL of 0.1M mannose in the same buffer; this was the first eluted fraction (E1). Bound material was eluted with 0.5M ∂-methyl mannopyranoside in wash buffer, in portions of 0.8 mL (E2), 1.2 mL (E3), and 4–5 portions of 1.0 mL (E4–E9). Cathepsin Y was eluted as a broad peak between 0.8 and 6 mL of elution buffer.

Enzymatic Activity

Purified 31 kD protease (Cathepsin Y) was without effect on various APP preparations, including purified recombinant APP constructs as well as membrane-bound full-length APP. No significant activity was seen also with known synthetic substrates commonly used for assaying Cathepsin B, L or S. These results suggested that Cathepsin Y does not have the standard endopeptidic activity associated with such proteases. In an effort to identify whether the enzyme has other proteolytic activity, a number of randomly selected synthetic oligopeptides were incubated with purified Cathepsin Y at pH 5.5 or 4.5. Specifically, purified Cathepsin Y was incubated with the selected synthetic oligopeptides (50 μg/mnL) at either pH 4.5 or pH 5.5, for 1 hour at 37° C. Samples were quenched by the addition of trifluoroacetic acid to 1% final concentration, then analyzed by reverse phase HPLC on a Vydac C18 column, using a gradient of increasing acetonitrile in 0.1% trifluoroacetic acid. Individual peaks (parent and new product(s)) were collected, then analyzed by acid hydrolysis followed by amino-acid analysis. The results are summarized below:

| Parent Sequence | Product(s) |
| --- | --- |
| LFYDQSPTATI (SEQ ID NO: 5) | LFYDQSPTAT (aa 1–10 of SEQ ID NO: 5) |
| | LFYDQSPTA (aa 1–9 of SEQ ID NO: 5) |
| | LFYDQSPT (aa 1–8 of SEQ ID NO: 5) |
| YKRDMVGGVVIA (SEQ ID NO: 6) | YKRDMVGGVVI (aa 1–11 of SEQ ID NO: 6) |
| | YKRDMVGGVV (aa 1–10 of SEQ ID) NO: 6) |
| EGYYGNYGV (ammo acids 1–9 of SEQ ID NO: 7) | EGYYGNYGV (aa 1–9 of SEQ ID NO: 7) |
| EGYYGNYGVYA (SEQ ID NO: 7) | EGYYGNYGVY (aa 1–10 of SEQID NO: 7) |
| | EGYYGNYGV (aa 1–9 of SEQ ID NO: 7) |
| FFDEPNPGVTIY (SEQ ID NO: 8) | FFDEPNPGVT (aa 1–10 of SEQ ID NO: 8) |

[The above peptides, as well as other peptides recited herein, are listed, per convention, from amino terminus to the carboxyl terminus.]

The results from a number of such experiments (all not shown) suggest that the only proteolytic activity of Cathepsin Y is a sequential removal of the carboxy terminal amino-acids which is direct evidence for carboxypeptidase activity. No evidence of any endopeptidase or aminopeptidase activity was seen with any of these substrates. These data strongly suggest that the predominant proteolytic activity manifested by Cathepsin Y is carboxypeptidase activity.

The quantitative analysis of carboxypeptidase activity of Cathepsin Y is based on the detection of the new free amino-terminus generated on cleavage of a selected substrate. This is accomplished by reacting with the reagent o-phthalaldehyde in an alkaline solution in the presence of 2-mercaptoethanol (Simons, et al., JACS, 98:7098–7099, (1976)). The peptide, EGYYGNYGV (aa 1–9 of SEQ ID NO:7), was synthesized acetylated on its amino-terminus so that on cleavage by Cathepsin Y, the only free amino-terminus will be present in the reaction mixture will be that of the valine residue, cleaved off by the carboxypeptidase activity of the protease.

Figure 7:
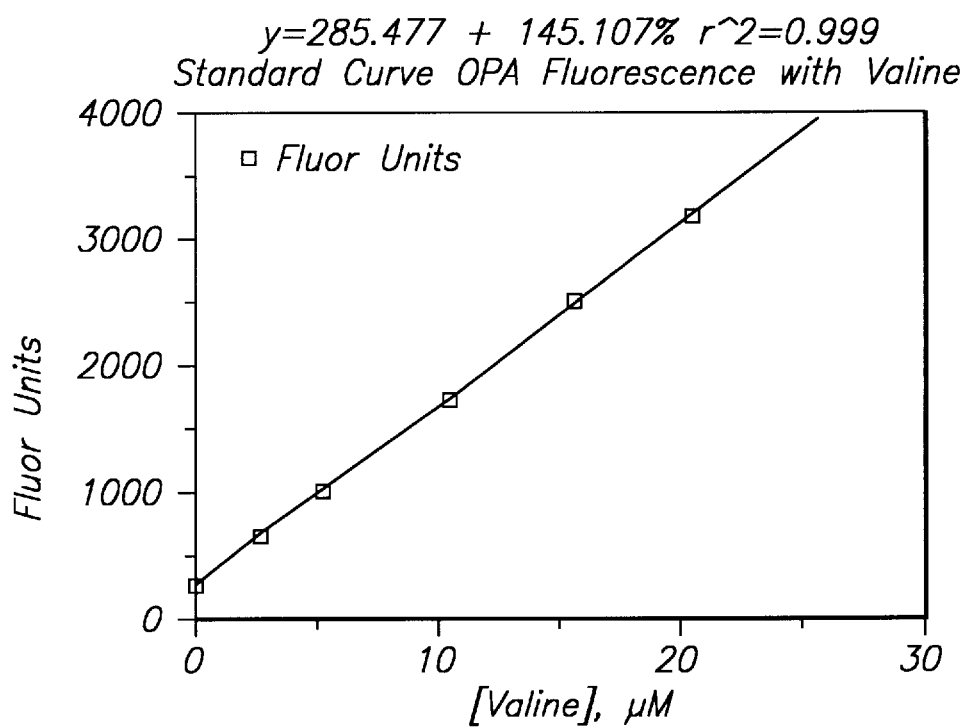
FIG. 7 illustrates a standard OPA curve for fluorescence with varying concentrations of valine.

A standard curve was constructed by incubating varying concentrations of valine (0–20 μM) in 0.25M sodium borate, pH 10, containing 0.05% 2-mercaptoethanol and 60 μg/mL o-phthalaldehyde, in individual wells of a 96 well microtiter plate. The resulting fluorescence is read in a plate reading Cytofluor (ex 340, em 460 nm). There is a linear increase in the signal proportional to the amount of free valine present (FIG. 7).

In order to determine the pH optimum of the enzyme, reaction mixtures were set up with enzyme and substrate (0.2 mg/mL) in a total reaction volume of 0.1 mL) in individual wells of 96-well microtiter plates, in 20 mM sodium acetate buffers at different pHs, with 0.1% 2-mercaptoethanol present. Control wells were set identically except for the presence of enzyme. At various timepoints after incubation at room temperature, the reactions were quenched by the addition of an equal volume of 0.45M sodium borate, pH 10, with 0.25 mg/mL o-phthalaldehyde, and the fluorescence measured. In the absence of added enzyme, no measurable fluorescence is generated above background, even with extended incubations. In the presence of enzyme, there is a time-dependent increase in fluorescence. Based on this analysis, the pH optimum for carboxypeptidase activity was determined to be about 4.5, with the activity dropping off at both lower and higher pHs.

Using this assay at pH 4.5, the ability of a number of compounds to inhibit the activity of Cathepsin Y was tested, by adding the desired concentration of the inhibitor in the incubation mixture along with enzyme and substrate, and measuring the decrease in fluorescence (if any) relative to enzyme control. Each of the compounds of Examples 3, 4, 7, 15, 24, 45, 47, 59, 64 and 75 tested in this analysis indicated inhibition of Cathepsin Y activity.

Protein Sequence Analysis

Direct sequencing of the 31 kD protein band following electroblotting onto PVDF membranes revealed the following sequence (SEQ ID No. 4):

(S) L P K S W (G,D) (N,V) R N V D G (V,N) N Y A S I (R,T)

Residues in parentheses are uncertain amino acid assignments. However, this limited amino-terminal sequence information showed clear homology to a known cysteine protease, rat Cathepsin C, which suggested that this new enzyme may belong to the papain superfamily of cysteine proteases, which also includes the cathepsins B, L and S. Therefore, degenerate oligonucleotide primers were designed using known conserved sequences in the cysteine proteases and from the newly discovered amino-terminal sequence, in order to use PCR to clone out the new enzyme.

Cathepsin Y Cloning

To obtain an initial DNA clone of this protease, degenerate PCR was performed using degenerate oligonucleotides encoding the amino acids of this newly discovered amino-terminal sequence and encoding oligonucleotide sequences conserved in the cystein proteases of the papain family. cDNA was made from RNA of human HS683 (human glioma cell line: ATCC #HTB138) cells using the Perkin Elmer GeneAmp RNA PCR kit as described by the manufacturer and denatured in a boiling water bath. The PCR reaction contained 1 μg of poly A+ RNA, 1× Perkins-Elmer-Cetus PCR buffer 1, 25 pM of each of oligonucleotides "Acys5" and "I Mer5"

Acys5 (SEQ ID NO:9)=TG.TAC.CCG.GGC.(AGC)(TC)A.(AG)CA.IGA.(AT)CC.G encoding amino acids CGSC(YW) (SEQ ID NO:10)

I Mer5 (SEQ ID NO:11)= C.GTA.GGA.TCC.CTI.CCX.AA(GA).AGC.TGG encoding amino acids (S)LPKSW (SEQ ID NO:12) 50 μM each dNTP, and 0.5 units Taq polymerase in the 25 μL total volume. The PCR reaction was subjected to 30 cycles each consisting of 95° C. for 45 seconds, 45° C. for 1.5 minutes, a slow 1 minute rise in temperature up to 70° C., and 70° C. for 30 seconds followed by 8 minutes at 72° C. Acrylamide gel electrophoresis displayed multiple PCR products so the entire PCR reaction was subcloned and multiple clones sequenced. One out of 82 clones examined, hCatZ.82 (nucleotides 299–366 of SEQ ID NO:2) encoded the amino acids of this newly discovered amino-terminal sequence.

A larger DNA clone of Cathepsin Y was obtained by degenerate PCR using sequence from hCatZ.82 (nucleotides 299–366 of SEQ ID NO:2) and conserved sequences of the cystein proteases of the papain family. PCR oligonucleotides used were 1683 (nucleotides 298–319 of SEQ ID NO:2)=5'. . . TGG.GAC.TGG.CGC.AAT.GTG.GAT.G . . . 3' and LM#4 (also called Bcys2) (SEQ ID NO:13)=5'. . . GAC.TGA.ATT.CTT.NAC.NAG.CCA.GTA . . . 3'.

```
dT17 + adapter for first strand synthesis:
    primer-1576 (SEQ ID NO: 16) =
        5'-GGA CTC GAG TCG ACT CTA GAG CGT TTT TTT TTT
    TTT TTT TT-3'

Adapter (XhoI-SalI-XbaI):
    primer-1577 (SEQ ID NO: 17) =
        5'-GAC TCG AGT CGA CTC TAG AGC GT-3'
```

The conditions for cDNA synthesis and PCR were as described above except that the annealing temperature was increased to 50° C. and the 70° C. extension incubation was for 45 seconds. The PCR reaction yielded a single 528 bp band which was subcloned and sequenced, and the sequence of the resulting clone (CatZ(+)3) (nucleotides 299–867 of SEQ ID NO:2) is indicated in FIGS. 4A–4E.

To obtain further 5' sequence, PCR reactions were performed on phage from a HeLa cell cDNA library (in lambda zap 2 vector from Stratagene). 5 μL of phage at 1×10^10 phage/mL were boiled for 2 minutes and placed on ice. Hot Start PCR was performed according to the manufacturer (Perkin Elmer/Cetus) using oligonucleotide

RACE31-NC (SEQ ID NO:20)=CAG GAG GGT GGA GGG CCA CGC TCC CT and an oligonucleotide corresponding to the lambda vector (788-1)

788-1 (SEQ ID NO:14)= GGAAACAGCTATGACCATGAT under the following conditions; 50 pM RACE31-NC oligonucleotide (SEQ ID NO:20), 25 pM of 788-1 oligonucleotide (SEQ ID NO:14), 1×PCR buffer II, 100 μM dNTPs, 2.5 mM MgCl$_2$, and 1.25 units of Taq polymerase in a reaction volume of 50 μL. The reaction was heated to 80° C. for 10 minutes and then subjected to 30 cycles of 94° C. for 1 minute, 55° C. for 45 seconds, a 1 minute ramp up to 72° C. and 1 minute at 72° C., followed by a final single extension at 72° C. for 8 minutes. A second nested Hot Start PCR reaction was done under the same conditions on 1 μL of the PCR products using 25 pM of an oligonucleotide corresponding to the lambda vector (872)

872 (SEQ ID NO:15)=CCC.TCA.CTA.AAG.GGA.ACA and 50 pM oligonucleotide NestR31-nc (reverse complement of nucleotides 385–411 of SEQ ID NO:2)). Southern analysis on the PCR products with oligonucleotide 1705 (nucleotides 301–366 of SEQ ID NO:2) as a probe displayed reactive products and PCR products of the appropriate size. These were subcloned and clones containing a diagnostic ApaI site (shown at nucleotides 380–385 of SEQ ID NO:2) of FIGS. 4A–4E were sequenced and the sequence of clone cat Y P3-25 (nucleotides 202–411 of SEQ ID NO:2) is shown on FIGS. 4A–4E.

In order to obtain additional 3' and 5' sequence of this clone, 3' and 5' RACE PCR techniques were used (Frohman et al., (1988), *PNAS USA* 85:8998–9002.)

For 3' RACE reactions cDNA was synthesized from polyA+RNA from human HS683 cells (Frohman et al., (1988) *PNAS USA* 85:8998–9002) using the cDNA synthesis conditions in Clontech 5' AmpliFINDER ™RACE kit protocol with the following modifications: 2 μg of RNA was used in 100 μL volume and the adaptor primer described below was used to prime synthesis. The adapter primers were a modification of that described by Frohman, et.al, (1988), *PNAS USA* 85:8998–9002.

Hot Start PCR was performed using the adapter primer 1577 and internal primer Nestr31-c (FIGS. 4A–4E) (nucleotides 343–366 of SEQ ID NO:2) at an annealing temperature of 55° C. Hot Start conditions were modifications of Perkin-Elmer AmpliWax™ protocol. Final concentrations of all reagents, after combining both layers: Lower mix is 1.25×PCR buffer (10×PCR buffer II [Perkin Elmer Cetus, Norwalk, Conn.] is 500 mM KCl, 100 mM Tris-HCl pH8.3), 2 mM MgCl$_2$ (Perkin Elmer Cetus), 200 μM dNTP (Perkin Elmer Cetus), 1 μM each primer in total volume of 12.5 μL. Upper mix is 1.25×PCR buffer, 1.25U AmpliTaq® DNA Polymerase (Perkin Elmer Cetus), 1 μL template DNA in 37.5 μL total volume. Ampliwax® PCR Gem 50 (Perkin Elmer Cetus) is added to the lower mix which is brought to 80° C. for 5 minutes, then held at 25° C. until the addition of the upper mix. PCR conditions included initial denaturation at 95° C. for 2 minutes followed by 30 cycles of 94° C. for 45 seconds, 55° C. for 45 seconds, 72° C. for 2 minutes, and then a final single extension at 72° C. for 8 minutes.

Southern blot analysis of RACE reactions using radiolabelled oligonucleotide 1758 (nucleotides 553–577 of SEQ ID NO:2) (FIGS. 4A–4E) as probe showed bands at approximately 800 and 1100 bp. These bands were gel-isolated and cloned into pT7Blue (Novagen, La Jolla, Calif.). Novablue cells (Novagen, LaJolla, Calif.) were transformed and colonies positive for Cathepsin Y sequence by PCR analysis were sequenced. The larger fragment proved to contain the stop codon and polyA tail, and its sequence is shown on FIGS. 4A–4E (indicated in FIG. 4 by "3'RACE") (nucleotides 343 to 1558 of SEQ ID NO:2).

All 5'RACE reactions were done from 5'RACE-Ready® human liver cDNA (Clontech). The cDNA is generated by random-priming and is provided with an anchor sequence ligated to the amino terminus.

CLONTECH Anchor region (SEQ ID NO:18):
3'-NH$_3$-GGAGACTTCCAAGGTCTT-AGCTATCACTTAAGCAC-P-5'

Anchor primers:
primer - 1821 (SEQ ID NO:19)=5'-CTGGTTCGGCCCACCTCTGAAGGTTCCAG-AATCGATAG-3'
primer - 1823 (nucleotides 14–38 of SEQ ID NO:19) =5'-CCTCTGAAGGTTCCAGAATCGATAG-3'

To obtain a clone encoding region 1 (FIGS. 4A–4E) (nucleotides 175–411 of SEQ ID NO:2), PCR was done under the above Hot Start conditions with oligonucleotides NestR31-nc (FIGS. 4A–4E) (reverse complement of nucleotides 385–411 of SEQ ID NO:2) to 1821 (SEQ ID NO:19) using 65° C. annealing temperature. PCR conditions included initial denaturation at 94° C. for 2 minutes; then 35 cycles of 94° C. for 45 seconds, 60° C. for 45 seconds, 72° C. for 2 minutes and then a final extension at 72° C. for 8 minutes.

A Southern blot was probed with $^{32}$P-kinased oligonucleotide 1810 (FIGS. 4A–4E). DNA of corresponding size was gel-isolated and cloned directly into pT7Blue. Novablue cells (Novagen, LaJolla, Calif.) were transformed and colonies positive for Cathepsin Y sequence by PCR analysis with the largest inserts were sequenced. One clone of 63 screened contained the sequence identified as region 1 (nucleotides 175–411 of SEQ ID NO:2).

To obtain a clone encoding region 2 (nucleotides 133–270 of SEQ ID NO:2), primary PCR was done using the above Hot Start conditions (with the subsitution of 7-deaza-GTP:GTP at a ratio of 3:1 instead of standard GTP in the DNTP mix) with oligonucleotides 1685 (FIGS. 4A–4E) (nucleotides 316–348 of SEQ ID NO:2) and 1821 (SEQ ID NO:19), annealing at 60° C. PCR conditions included initial denaturation at 95° C. for 2 minutes, followed by 35 cycles of 95° C. for 45 seconds, 60° C. for 45 seconds, 72° C. for 1.5 minutes, and then a single final extension at 72° C. for 8 minutes. PCR products run on a 2% agarose gel showed a smear of DNA. DNA greater than 200 bp in size was isolated and purified using Geneclean™ (Bio 101, Madison, Wis.). This DNA was used as a template for nested PCR using oligonucleotides 1810 (FIGS. 4A–4E) (nucleotides 243–270 of SEQ ID NO:2) and 1823 (nucleotides 14–38 of SEQ ID NO:19) under the above Hot Start conditions with the addition of 1 µL of single-strand binding protein (USB) in the lower layer along with the template DNA and Hot Start temperature of 95° C. rather than 80° C. The primers were added to the upper mix, and PCR proceeded with annealing at 60° C. A Southern blot of the PCR product was probed with $^{32}$P-kinased oligonucleotide 1846 (FIGS. 4A–4E) (nucleotides 175–204 of SEQ ID NO:2) and appropriate sized DNA was isolated from the gel, ligated into pT7Blue, and transformed into SURE cells (Stratagene, La Jolla Calif.). 7 colonies were positive for Cathepsin Y sequence by PCR analysis out of 27 screened. The one clone sequenced contained the sequence identified as region 2 (FIGS. 4A–4E) (nucleotides 133–270 of SEQ ID NO:2).

To obtain a clone encoding region 3, primary PCR was done and template for secondary PCR was prepared as for region 2 (nucleotides 133–270 of SEQ ID NO:2), but using oligonucleotide NestR31-nc (FIGS. 4A–4E) (reverse complement of nucleotides 385–411 of SEQ ID NO:2) instead of 1685 (nucleotides 316–348 of SEQ ID NO:2). Secondary PCR was done using oligonucleotides Kyl (FIGS. 4A–4E) (nucleotides 140–159 of SEQ ID NO:2) and 1823 (nucleotides 14–38 of SEQ ID NO:19) under standard Hot Start conditions but with the addition of 1 µL of single-strand binding protein in the lower layer along with the DNA template, then a Hot Start temperature of 100° C. for one minute. Deep Vent DNA Polymerase (NEB) was used for PCR which allowed denaturation at 100° C., instead of 94°–95° C. For Vent PCR, Perkin-Elmer PCR buffer and MgCl$_2$ were replaced by NEB 10× Vent polymerase buffer (100 mM KCl, 200 mM Tris-HCl pH 8.8, 100 mM NH$_4$]$_2$SO$_4$, 20 mM MgSO$_4$, 1.0% Triton X100) at the appropriate concentrations. Deep Vent$_R$® DNA Polymerase (NEB) was used at 2U per 50 µL reaction. Annealing was done at 60° C. The PCR product was blunt ended with Klenow, digested with EcoRI and gel purified. Fragments of 100–150 bp and 150–200 bp were isolated separately and ligated into EcoRI/EcoRV digested pBR322. SURE cells were then transformed and colonies positive for Cathepsin Y sequence by PCR analysis with the largest inserts were sequenced yielding clones containing the sequence indicated as region 3 in FIGS. 4A–4E (nucleotides 0–159 of SEQ ID NO:2).

Northern analysis under stringent conditions show that in various tissue and cell sources a single sized mRNA species of approximately 1600 bp encodes Cathepsin Y. Thus even though some sequences in FIGS. 4A–4E are from differing sources (Hs683 and liver) it is thought that the sequence of Cathepsin Y is not significantly different among those sources. The above techniques have been used to identify additional independently derived clones from various sources that verify the validity and contiguity of the sequence shown in FIGS. 4A–4E. The size encoded by the sequence in FIGS. 4A–4E is sufficient to encode the entire mRNA, and the open reading frame indicated starts with a signal peptide as would be expected for a cystein protease of the papain family. This indicates that this is the entire encoding region of Cathepsin Y.

Cathepsin Y Expression

Figure 5:
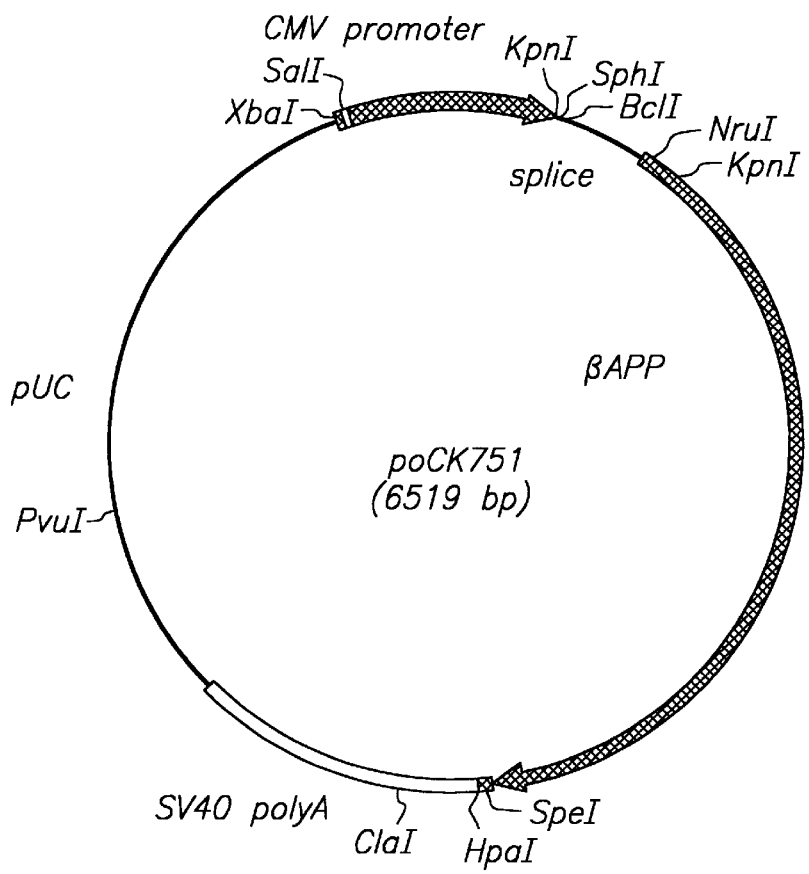
FIG. 5 shows the restriction map of plasmid poCK751.
Figure 6:
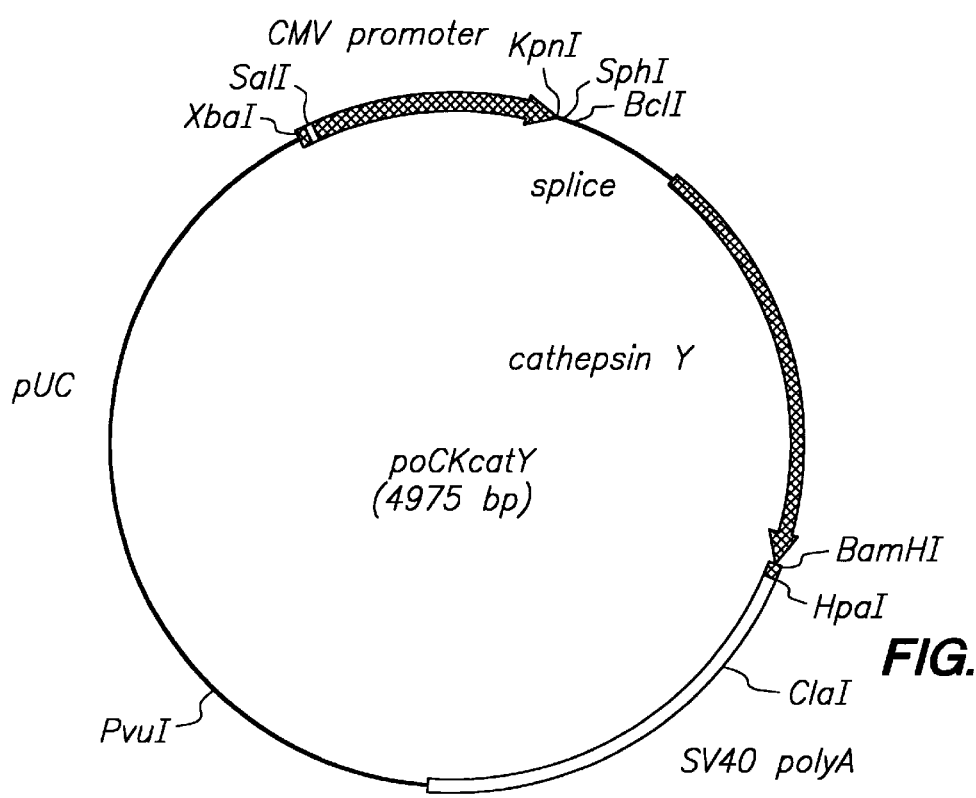
FIG. 6 shows the restriction map of plasmid poCKcatY.

The BamHI fragment containing the entire coding region of the Cathepsin Y was blunt ended and cloned into the vector poCK751 cut with NruI and SpeI (blunt ended) (FIG. 5) so that the βAPP sequences were removed and replaced with those of Cathepsin Y to form the plasmid poCK catY (FIG. 6).

Transfection of this resulting plasmid using the Boheringer Mannheim DOTAP transfection kit into human 293 kidney cells resulted in the expression of active Cathepsin Y protein. This indicates that this clone encodes the entire coding region of Cathepsin Y, and that active Cathepsin Y protein can be generated from this clone.

Varying amounts of Cathepsin Y cDNA in the poCK expression vector were transfected transiently into 293 cells, in 6 well plates. Transfection was carried out using DOTAP (Boehringer Mannheim), using protocols suggested by the manufacturer. 48–72 hours following transfection, the cells were washed with cold PBS, then lysed in 1 mL of 20 mM MES, pH 6, 0.1% Brij-35, 2 mM EDTA. 10 µL aliquots of the lysate (following centrifugation to remove cell debris) were electrophoresed using SDS-PAGE, followed by transfer of the proteins onto a PVDF membrane. The membrane was probed with the anti-cathepsin B antibody for Western blot analysis. A dose-dependent increase in the ~31 kDa immunoreactive Cathepsin Y band was seen as a result of transient expression of the Cathepsin Y cDNA.

300 µL of the lysates were then absorbed with 20 µL of the Val-Phe-aldehyde affinity matrix. This resulted in complete loss of the ~31 kDa immunoreactive Cathepsin Y band from the cleared lysates, indicating that the overexpressed protein is active and competent to bind to the inhibitor affinity matrix. Elution of the matrix with DPDS showed that there was a DNA dose-dependent increase in Cathepsin Y carboxypeptidase activity in the transfection studies. The increase in expression directly correlated with the amount of cDNA transfected into the cells.

These data confirm that expression of the cDNA clone for Cathepsin Y results in overexpression of enzymatically active Cathepsin Y, migrating on SDS-PAGE at ~31 kDa, and able to bind and elute from the inhibitor affinity matrix.

Although the foregoing invention has been described in detail for purposes of clarity of understanding, it will be obvious that certain modifications may be practiced within the scope of the appended claims.

What is claimed is:

1. A method of inhibiting β-amyloid peptide production in cells producing β-amyloid peptide, comprising administering to such cells an inhibitory amount of a compound of formula I:

wherein:
R is selected from the group consisting hydrogen, alkyl of from 1 to 6 carbon atoms, and where R and $R^2$ are joined to form a ring structure of from 4 to 10 carbon atoms, R' is selected from the group consisting hydrogen, alkyl of from 1 to 6 carbon atoms and where R' and $R^3$ are joined to form a ring structure of from 4 to 10 carbon atoms, $R^1$ is selected from the group consisting of
  alkyl of from 1 to 4 carbon atoms substituted with 1 substituent selected from the group consisting of (a) aryl of from 6 to 10 carbon atoms, (b) aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino, (c) cycloalkyl of from 3 to 8 carbon atoms and (d) heterocycles of from 3 to 14 carbon atoms having from 1 to 3 heteroatoms selected from the group consisting of nitrogen, oxygen and sulfur
  wherein said substituted alkyl group is optionally further substituted with from 1 to 2 hydroxyl groups,
  aryl of from 6 to 10 carbon atoms,
  aryl of from 6 to 10 carbon atoms substituted with 1 to 3 substituents selected from the group consisting of alkyl of from 1 to 6 carbon atoms, aryl of from 6 to 10 carbon atoms, alkoxy of from 1 to 6 carbon atoms, aryloxy of from 6 to 10 carbon atoms, hydroxy, cyano, halo and amino,
  heterocycles of from 3 to 14 carbon atoms having from 1 to 3 heteroatoms selected from the group consisting of nitrogen, oxygen and sulfur;

$R^2$ and $R^3$ are independently D- or L-amino acid side chains of at least 2 carbon atoms with the proviso that said amino acid side chains do not include the proline side chain;

$R^4$ is selected from the group consisting of
  —C(O)$R^5$ where $R^5$ is hydrogen, alkyl of from 1 to 6 carbon atoms, and haloalkyl of from 1 to 6 carbon atoms and 1 to 2 halo groups;

X is selected from the group consisting of —O—, —$NR^9$—, and —S— where $R^9$ is selected from the group consisting of hydrogen, alkyl of from 1 to 6 carbon atoms and aryl of from 6 to 10 carbon atoms;

Y is selected from the group consisting of —C(O)— and —C(S)—;

m is equal to zero or one; and n is equal to zero to two, or pharmaceutically acceptable salts thereof with the proviso that when $R^1$ is 1-naphthyl, $R^2$ is —CH(CH$_2$)$_2$ (L-isomer), $R^3$ is —CH$_2$φ (L-isomer), Y is —C(O)—, m is zero and n is one, then $R^4$ is not —N(CH$_3$)OCH$_3$, with the further proviso that when $R^1$ is diphenylmethyl, $R^2$ is p-(benzyloxy)benzyl (L-isomer), Y is —C(O)—and m and n are zero, then $R^4$ is not —N(CH$_3$)OCH$_3$, and with still the further proviso that when $R^1$ is (1,2-diphenyl)ethenyl, Y is —C(O)—, $R^2$ is —CH$_2$φ (L-isomer), and m and n are zero, the $R^4$ is not —N(CH$_3$)OCH$_3$.

2. The method of claim 1, wherein $R^1$ is selected from the group consisting of benzyl, 4-phenylbutyl, 2-phenylethyl, naphthyl, and pyridyl.

3. The method of claim 1, wherein $R^2$ is selected from the group consisting of the d- and l-isomers of valine, leucine, phenylalanine, tryptophan and isoleucine.

4. The method of claim 1, wherein $R^3$ is selected from the group consisting of the d- and l-isomers of valine, leucine, phenylalanine, tryptophan and isoleucine.

5. The method of claim 1, where $R^4$ is —C(O)H.

6. The method of claim 1, wherein said compound is

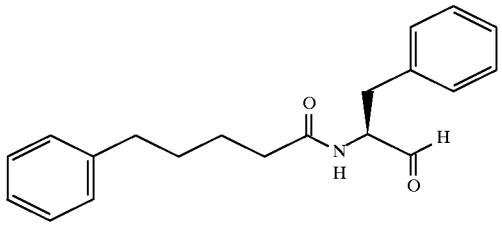

7. The method of claim 1, wherein said compound is

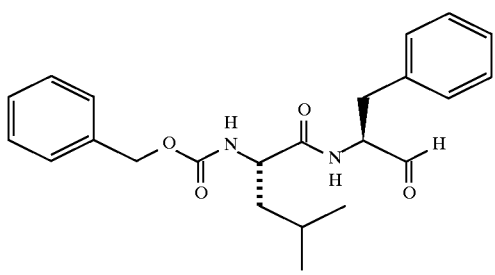

8. The method of claim 1, wherein said compound is

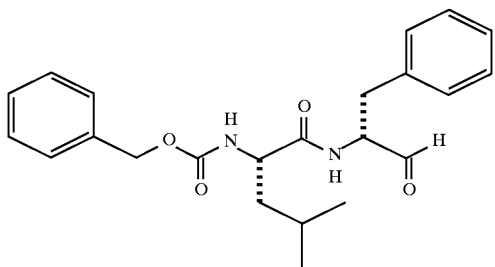

9. The method of claim 1, wherein said compound is

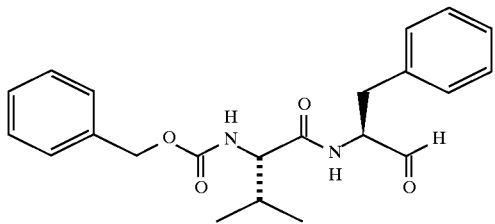

10. The method of claim 1, wherein said compound is

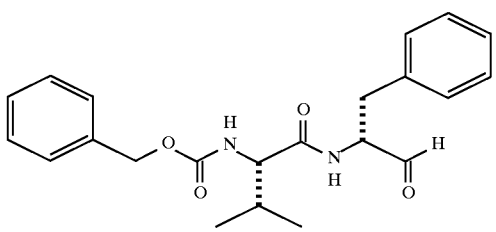

11. The method of claim 1, wherein said compound is

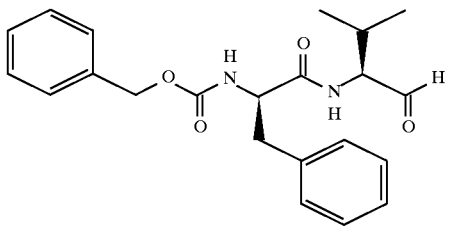

12. The method of claim 1, wherein said compound is

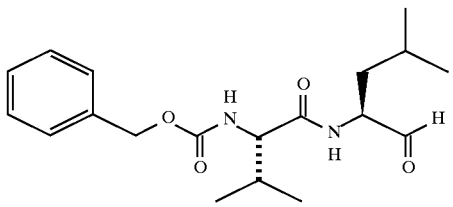

13. A method of inhibiting the deposition of amyloid plaque in a mammal, comprising administering to such mammal an effective amount of a compound of Formula I as defined in claim 1.

* * * * *